(12) United States Patent
Plante

(10) Patent No.: US 6,520,987 B1
(45) Date of Patent: Feb. 18, 2003

(54) EXPANDABLE INTRAVASCULAR STENT

(75) Inventor: Sylvain Plante, Ste-Foy (CA)

(73) Assignee: Symbiotech Medical, INC, Ile Perrot (CA)

(*) Notice: Subject to any disclaimer, the term of this patent is extended or adjusted under 35 U.S.C. 154(b) by 0 days.

(21) Appl. No.: 09/382,802

(22) Filed: Aug. 25, 1999

Related U.S. Application Data

(63) Continuation of application No. PCT/CA98/00140, filed on Feb. 25, 1998.

(30) Foreign Application Priority Data

Feb. 25, 1997 (GB) ............................................. 9703859
Mar. 25, 1997 (CA) ............................................. 2201001

(51) Int. Cl.⁷ ................................................. A61F 2/06
(52) U.S. Cl. .................................... 623/1.16; 623/1.35
(58) Field of Search ............................. 623/1.15, 1.16, 623/1.35, 1.17, 1.18, 1.19, 23.7

(56) References Cited

U.S. PATENT DOCUMENTS

| | | |
|---|---|---|
| 5,102,417 A | 4/1992 | Palmaz |
| 5,135,536 A | 8/1992 | Hillstead |
| 5,195,984 A | 3/1993 | Schatz |
| 5,354,308 A | 10/1994 | Simon et al. |
| 5,382,261 A | 1/1995 | Palmaz |
| 5,421,955 A | 6/1995 | Lau et al. |
| 5,609,627 A * | 3/1997 | Goicoechea et al. ........ 623/1.35 |
| 5,669,924 A * | 9/1997 | Shaknovich ................ 623/1.35 |
| 5,879,381 A * | 3/1999 | Moriuchi et al. ........... 623/1.16 |
| 5,906,640 A * | 5/1999 | Penn et al. ................. 623/1.35 |
| 6,013,091 A * | 1/2000 | Ley et al. .................. 623/1.16 |
| 6,042,606 A * | 3/2000 | Frantzen ................... 6223/1.18 |
| 6,309,414 B1 * | 10/2001 | Rolando et al. ............ 623/1.15 |

FOREIGN PATENT DOCUMENTS

| | | |
|---|---|---|
| EP | 0 540 290 A | 5/1993 |
| EP | 0 679 373 A2 | 11/1995 |
| WO | WO 96/14028 | 5/1996 |
| WO | WO 96/34580 | 11/1996 |

* cited by examiner

*Primary Examiner*—Paul B. Prebilic
(74) *Attorney, Agent, or Firm*—Swabey Ogilvy Renault

(57) ABSTRACT

An intravascular flexible permanent prosthesis (stent) for implantation in a body lumen such as an artery, consists of a plurality of radially expandable and deformable thin-walled ring elements aligned in a common longitudinal axis, and held together by interconnecting links so as to limit longitudinal expansion or contraction during radial deployment. The stent is delivered and expanded within a blood vessel by an angioplasty balloon catheter. The ring elements are formed of a series of hexagonal components or inverted hexagonal components, with elements of a series of hexagonal components preferably alternating with elements formed of a series of inverted hexagonal components. Each point of adjacent ring elements is adjoined by a pair of diametrically opposed links, whilst the succeeding pair of adjacent ring elements is adjoined by a pair of links which are diametrically opposed and located at an angle of 90° to the previous pair of links.

14 Claims, 25 Drawing Sheets

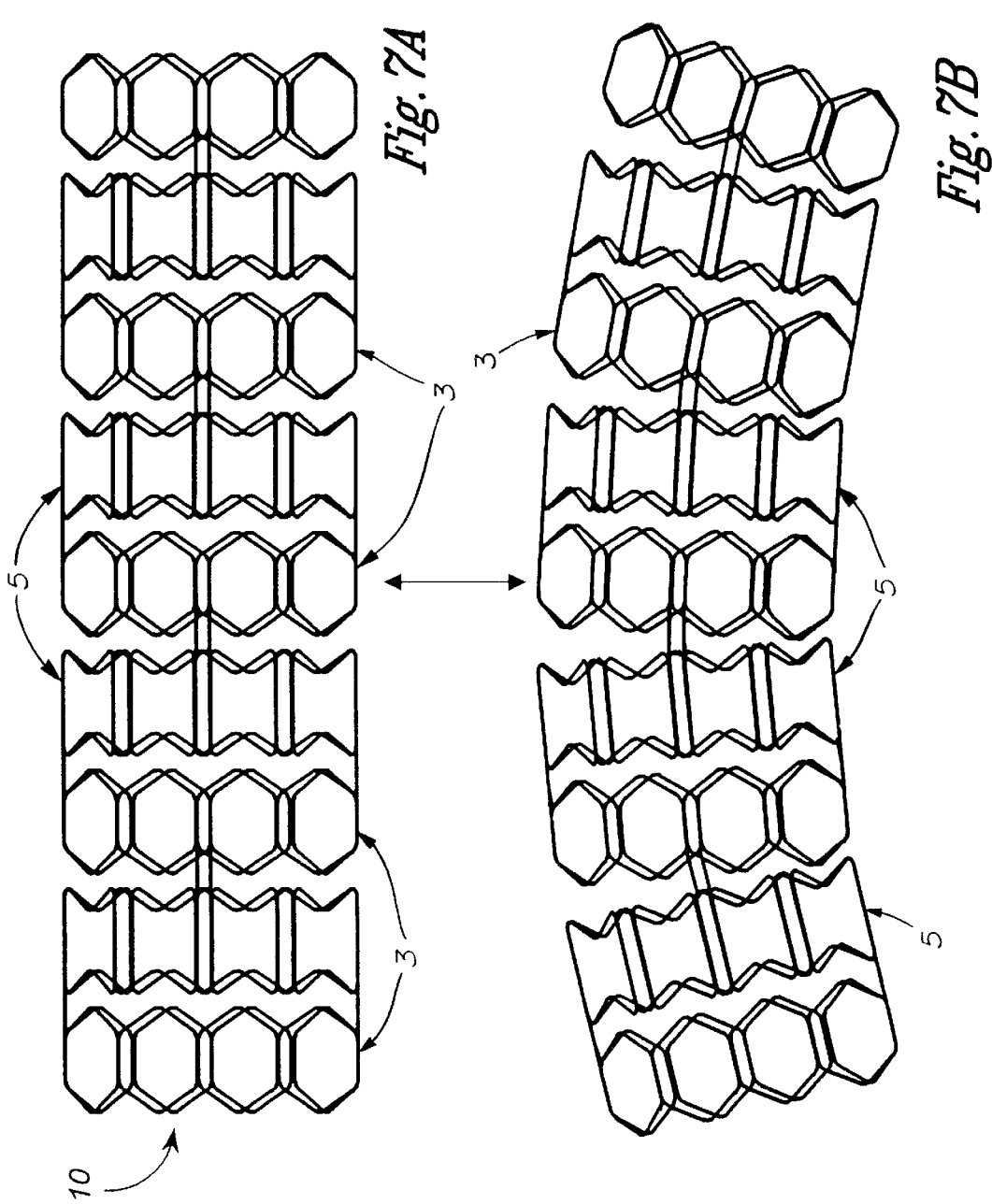

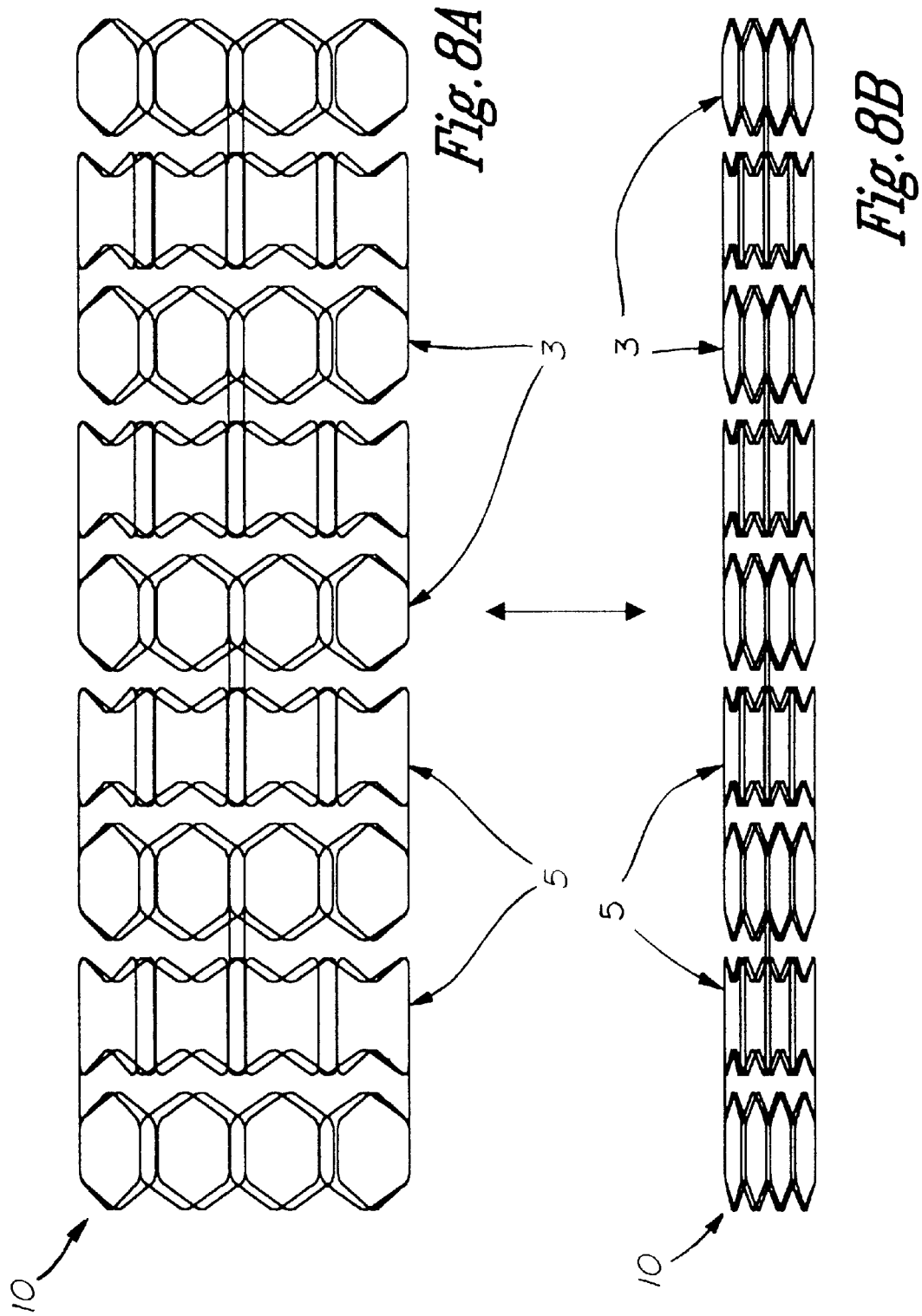

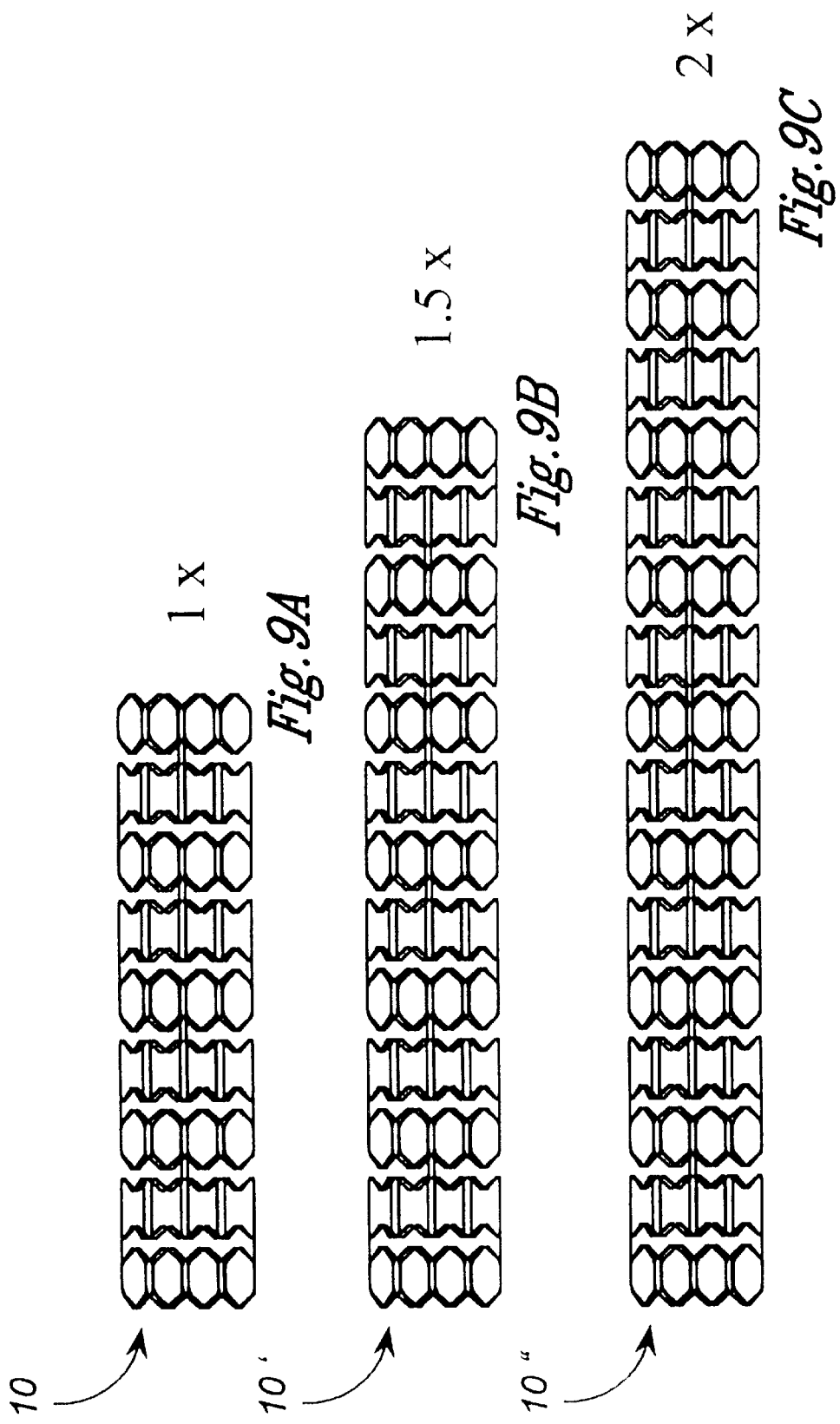

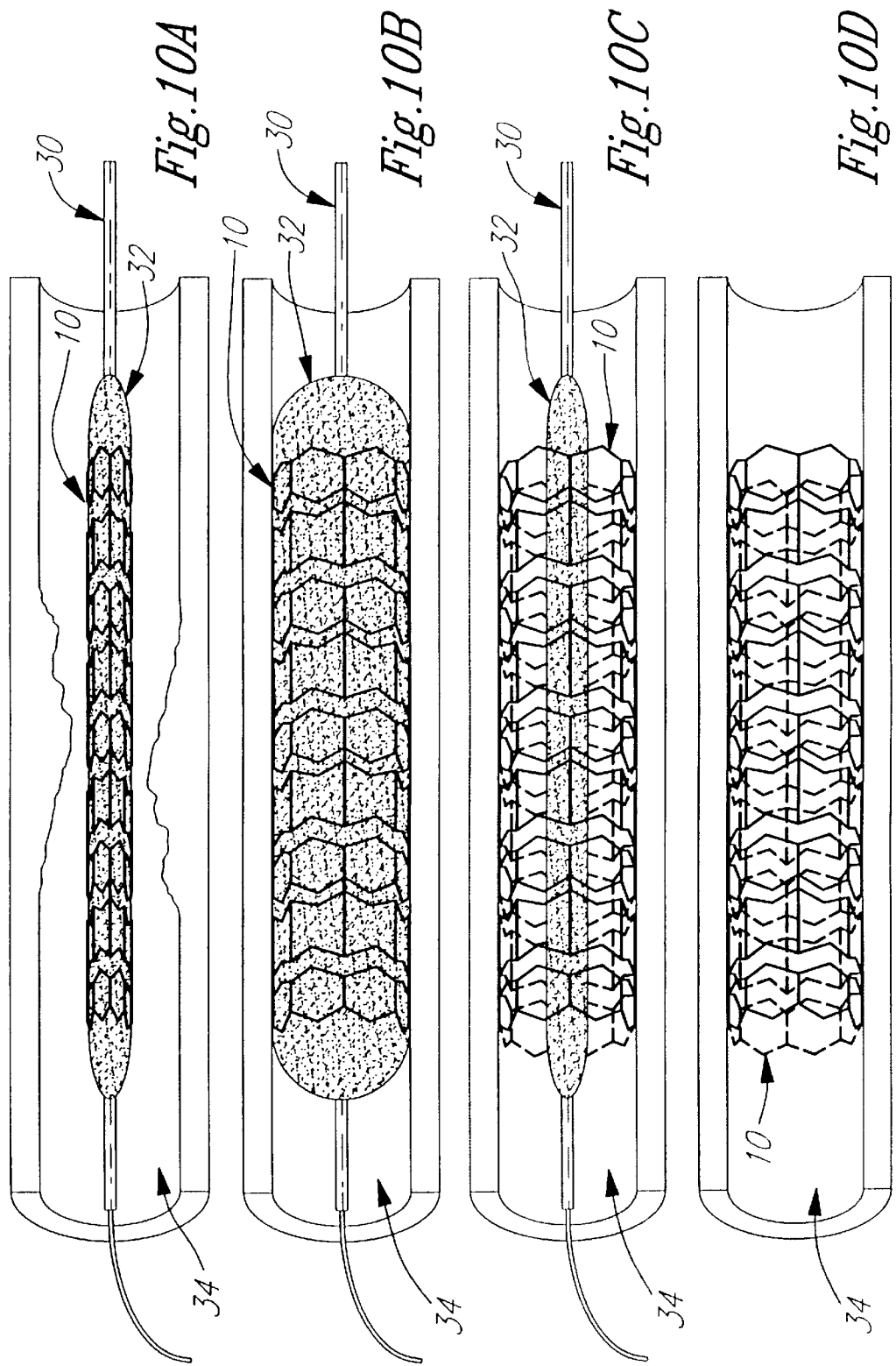

EXPANDABLE INTRAVASCULAR STENT

RELATED APPLICATIONS

This application is a continuation of PCT/CA98/00140 filed Feb. 25, 1998 designating the United States and claiming priority on British Patent Application serial number 9703859 filed Feb. 25, 1997 and on Canadian Patent Application serial number 2,201,001 filed Mar. 25, 1997.

BACKGROUND OF THE INVENTION

1.—Field of the Invention

This invention generally relates to expandable intravascular prosthetic devices, also known as stents, that are usually implanted in a patient s body lumen such as an artery to maintain the patency of the lumen after balloon angioplasty.

2.—Description of the Prior Art a) Stents in Clinical Practice

Stents are usually cylindrically shaped devices which function is to maintain patency or to expand a segment of a body lumen such as an artery. They are particularly useful for preventing a torn or injured arterial lining from occluding a fluid passageway, or for supporting a vessel segment in the presence of suboptimal results following balloon angioplasty. Coronary stenting is gaining widespread acceptance in the treatment of atherosclerotic coronary artery disease. Since the first report by Sigwart et al. of the placement of metallic stents in coronary arteries, coronary stenting has been shown to optimize the geometry of the coronary lumen after balloon angioplasty, to reduce procedural complications and the need for urgent coronary bypass surgery (as a bail-out strategy) and to decrease the rate of restenosis. Coronary stenting is considered by many interventional cardiologists as the therapy of choice for venous graft stenoses. This device is also increasing in popularity for de novo native coronary lesions (primary stenting). Two recent randomized clinical trials comparing stenting with standard balloon angioplasty in primary lesions have demonstrated the efficacy of the Palmaz-Schatz™ stent in reducing the rate of angiographically detected restenosis. In one of these trials, there was both angiographic and clinical benefit, as reflected by; a reduction in major clinical endpoints, especially repeated revascularization of the target lesion.

b) Types of Permanent Stents

Self-expanding Stents

The first stent available for clinical use consisted of a stainless-steel alloy with a self-expanding, spring-like mesh design. The stent was maintained in a constrained and elongated conformation at the distal portion of a delivery catheter by an overlying sheath. When released (by withdrawing the overlying sheath), the stent would automatically expand and increase to a final diameter dependent on the size of the stent and the elasticity of the artery wall. This type of stent is known as the Wallstent™. Although very flexible and providing excellent fluid dynamics, this self-expanding stent was found by some investigators to be deficient since, when deployed, it could exert an undue, permanent stress on the vessel wall. Moreover, significant longitudinal shortening is observed during radial self-expansion, which may result in inappropriate stent placement or inadequate dissection coverage.

Balloon-expandable Stents

The limitations encountered with the Wallstent™ lead to the development of various stents which were controllably expandable within a blood vessel. Generally, in these systems (often called "balloon-expandable stents") the stent, mounted and crimped on a deflated angioplasty balloon, is delivered to the target area of a blood vessel by a catheter system. Once the stent has been properly positioned (under fluoroscopic guidance), the balloon is expanded thereby expanding the stent so that the latter is urged in place against the vessel wall. At this point, the balloon is deflated, withdrawn and subsequently removed.

Balloon-expandable stents which have gained some notoriety are the Palmaz-Schatz™ stent, the ACS Multilink™ stent, the Wiktor™ stent and the Gianturco-Roubin Flex-Stent™. The Palmaz-Schatz™ and the ACS Multilink™ balloon expandable stents share the common design of a carved stainless-steel cylinder. The Palmaz-Schatz™ stent consists of two rigid stainless-steel slotted tubes joined by a single filament to aid in flexibility. The slotted configuration, when balloon-expanded, deploys as a meshwork. However, despite its articulation, the Palmaz-Schatz stent is known to lack flexibility for delivery in tortuous vessel anatomy and for expansion in angulated lesions. The ACS Multilink™ stent is somewhat similar to the latter, but differs in the increased number of bridges interconnecting identical corrugated rings. In comparison with the Palmaz-Schatz™ stent, the ACS Multilink™ stent has a better flexibility, a more operator-friendly delivery system and less longitudinal shortening during radial expansion.

The Wiktor™ stent, and the Gianturco-Roubin Flex-Stent™ share the common design of a monofilament wire wrapped around an angioplasty balloon catheter. Although they differ from each other in their material, coil structure, radiopacity and degree of wall coverage, they both offer a good flexibility for negotiating tortuous vessels and minimal longitudinal shortening during radial expansion. However, the major drawback is related to the hazard of inadvertent unraveling during manipulation and balloon withdrawal, due to their monofilament design. Other reported disadvantages are the relatively large wire spacing and some degree of recoil after expansion, which may be the reasons why restenosis after use of this type of stent is rather frequent.

All of the stents described above share the common design of being monotubular and thus best suited for delivery in the straight segment of a body passageway. These stents are inappropriate for placement in a bifurcation or a passageway having side branches since: a) the risk of closure of the side branch is increased and b) the side branch will be substantially inaccessible.

The presence of a bifurcation or a major side branch is well recognized as a contraindication for conventional stents.

Indeed, the Physician Guide published in support of the Palmaz-Schatz stent states: " . . . no attempt should be made following placement of a Palmaz-Schatz stent to access a side branch with a guide wire or a balloon, as such attempts may result in additional damage to the target vessel or the stent. Attempts to treat obstructed side branches within stented segments can result in balloon entrapment, necessitating emergency bypass surgery."

Thus, it would be desirable to have an expandable, steerable stent that could prevent obstruction and allow access to side branches, particularly in the field of interventional cardiology. It would be also desirable whether such a stent could be easy to install.

SUMMARY OF THE INVENTION

The present invention provides a longitudinally flexible permanent intravascular prosthesis, made of a plastically deformable metal alloy, for implantation in a body lumen and expandable from a contracted condition to an expanded condition, comprising: a plurality of adjacent rings independently expandable in the radial direction and interconnecting members between adjacent rings. The stent comprises two types of rings, each formed by a plurality of either hexagonal or inverted hexagonal elements. The two types of rings are arranged alternately in alignment over the longitudinal axis of the stent, so as to limit spacing between rings and to provide sufficient vessel wall coverage. Two interconnecting members are used to join adjacent rings, positioned at 0° and 180° in the transverse (cross-sectional) axis to provide flexibility between two rings in one plane; the next pair of interconnecting members is shifted 90° from the previous one to provide flexibility to the next attached ring in the perpendicular plane. Thus, this alternately interconnecting member disposition provides a relative flexibility along the longitudinal axis in either the contracted or the expanded state. This particular design has also the property to limit longitudinal expansion or contraction during radial deployment.

The stent is to be mounted and crimped over a balloon catheter, delivered in a contracted state within a body lumen such a patient s artery and expanded passively by the radial forces on the inflating balloon catheter.

A generally tubular stent according to the invention is formed from a deformable material and consists of a plurality of ring-shaped elements of the same radius joined together along a common axis, wherein adjacent ring elements each comprise at least two generally circumferential bands such that the ring element extends axially between a first end band and a second end band which are joined together by struts extending between them, with all of the bands having the same generally zigzag shape having at least three apices and three troughs around the circumference of the band, wherein the apices and troughs of adjacent first band of one ring element and second band of adjacent ring element are aligned on a straight line parallel to the axis, the ring elements being joined each by two links arranged generally parallel to the axis, the two links being radially spaced by an angle of about 180°, the pair of links joined to one end of each ring element being positioned radially at an angle in the range of 60° C. to 120° with respect to the pair of links joined to the other end of the respective ring elements, and wherein adjacent bands within each ring are arranged with apices of one and troughs of the other coinciding on a line parallel with the axis, the adjacent bands being joined by connectors joining each of the apices of one band to the respective trough (lying on the said line parallel to the axis) of the adjacent band of the ring element, or vice-versa, whereby the connectors and the portion of adjacent bands joined to connectors form a hexagonal shape with all. hexagonal shapes between a pair of adjacent bands having all internal angles less than 180° or having two opposite corners (defined by the bands) with angles greater than 180° and the remaining corners having angles less than 90°.

Each ring element preferably consists of a pair of bands joined together by respective connectors. In this embodiment, ring elements formed of bands joined by connectors to make hexagons having all internal angles less than 180° preferably alternate with ring elements formed as hexagons including two internal angles greater than 180° (each hereinafter referred to as an "inverted hexagon").

Alternatively a ring element may consist of three bands, with two adjacent bands forming regular hexagons with their respective connectors and with the other pair of adjacent bands forming inverted hexagons or with the other pair of adjacent bands forming regular hexagons. Alternatively three bands may be adapted to form with their connectors a series of inverted hexagons between both pairs of bands.

Each ring element may be formed of more than three bands, with any combination of regular hexagon series and inverted hexagon series within each ring element.

It is preferred for a series of regular hexagons around one end of a ring element to be opposed to a series of inverted hexagons at the adjacent end of the adjacent ring element. Where each element consists of a pair of bands, this result in alternating ring elements forming one series of regular hexagons and ring elements forming one series of inverted hexagons.

The stent generally consists of at least two articulated ring elements, preferably at least three articulated elements, for instance five or more ring elements.

The positioning of the links between adjacent pairs of ring elements, that is between 60° and 120°, gives the stent the freedom to bend at any angle between its ends. The ultimate effect is like that of a universal joint. Where there are only three ring elements therefore the angles between adjacent pairs of links should be about 90°. Where there are four or more ring elements, the angle may be as low as 60° or as high as 120°. Preferably, however, for every adjacent pair of links the angle between them is about 90°.

Preferably the stent is made from a circular cylindrical tube starting material from which material is removed, for instance by chemical or laser etching. Preferably the material is made from a metal, for instance a metal which can be plastically deformed, preferably by application of mechanical radially outwardly directed force, for instance by the use of a balloon. Alternatively, but less preferably, the stent may be made from shape memory alloy, such that the radius of the stent can be controlled by controlling the temperature of the stents environment.

The preferred embodiment in which each ring element of the stent consists of two bands with connectors joining the bands so as to form a series of regular hexagons or inverted hexagons with the two types of ring elements alternating with one another allows the spacing between ring elements to be minimized and optimizes vessel wall coverage. The provision of links between the rings at 180° optimizes longitudinal flexibility when the stent is unexpanded or in the expanded state. The inverted hexagonal elements limit longitudinal contraction during radial deployment.

Therefore the above present generally consists of a longitudinally flexible permanent prosthesis, made of a plastically deformable metal alloy, for implantation in a body lumen and expandable from a contracted condition to an expanded condition, comprising: a plurality of adjacent rings independently expandable in the radial direction and interconnecting members between adjacent rings. The stent comprises two types of rings, each formed by a plurality of either hexagonal or inverted hexagonal elements. The two types of rings are arranged alternately in alignment over the longitudinal axis of the stent, so as to limit spacing between rings and to provide sufficient vessel wall coverage. Two interconnecting members are used to join adjacent rings, positioned at 0° and 180° in the transverse (cross-sectional) axis to provide flexibility between two rings in one plane; the next pair of interconnecting members is shifted 90° from the previous one to provide flexibility to the next attached ring in the perpendicular plane. Thus, this alternately interconnecting member disposition provides a relative flexibility along the longitudinal axis in either the contracted or the expanded state. This particular design has also the property to limit longitudinal expansion or contraction during radial deployment. On the basis of this general stent design, the present invention also relates to the concept of "directional stenting", where a lateral opening is created in the, middle of the stent body, so that the lateral opening can be steered and aligned with the ostium of a bifurcation or a side branch, using a specific delivery system. The stent is to be expanded within a body passageway by the balloon catheter included in the delivery system.

Therefore, in accordance with the present invention, there is provided a generally tubular stent which is formed from a deformable material and consists of a plurality of ring-shaped elements of the same radius joined together along a common axis, wherein adjacent ring elements each comprise at least two generally circumferential bands such that the ring element extends axially between a first end band and a second end band which are joined together by struts extending between them, with all of the bands having the same generally zigzag shape having at least three apices and three troughs around the circumference of the band, wherein the apices and troughs of adjacent first band of one ring element and second band of adjacent ring element are aligned on a straight line parallel to the axis, the ring elements being joined each by two links arranged generally parallel to the axis, the two links being radially spaced by an angle of about 180°, the pair of links joined to one end of each ring element being positioned radially at an angle in the range of 60° to 120° with respect to the pair of links joined to the other end of the respective ring elements, and wherein adjacent bands within each ring are arranged with apices of one and troughs of the other coinciding on a line parallel with the axis, the adjacent bands being joined by connectors joining each of the apices of one band to the respective trough (lying on the said line parallel to the axis) of the adjacent band of the ring element, or vice-versa, whereby the connectors and the portion of adjacent bands joined to connectors form a hexagonal shape with all hexagonal shapes between a pair of adjacent bands having all internal angles less than 180° or having two opposite corners (defined by the bands) with angles greater than 180° and the remaining corners having angles less than 90°.

Also, in accordance with the present invention, there is provided an expandable prosthesis for a body passageway comprising a plurality of first and second ring-shaped members having ends of complementary shape, at least some of said first members longitudinally alternating with said second members, each pair of adjacent ring-shaped members being interconnected, at least one pair of adjacent alternating first and second members being flexibly connected together with at least one connecting member for allowing said adjacent first and second members to be articulated out of coaxial alignment, said first and second members each having a collapsed diameter for permitting delivery thereof in the body passageway and having at least one expanded diameter upon application from the interior of said first and second members of an outwardly directed force for expanding the body passageway.

Further in accordance with the present invention, there is provided an expandable prosthesis for a body passageway comprising a plurality of interconnected ring-shaped members, at least two pairs of adjacent ring-shaped members being flexibly connected together each with at least two diametrically opposed connecting members for allowing said pairs of adjacent members to be articulated out of coaxial alignment, said connecting members between a pair of adjacent ring-shaped members being angularly offset from adjacent connecting members, said ring-shaped members each having a collapsed diameter for permitting delivery thereof in the body passageway and having at least one expanded diameter upon application from the interior of said first and second members of an outwardly directed force for expanding the body passageway.

In a more specific construction, a side opening is defined laterally in at least two adjacent ring-shaped members of said prosthesis for positioning substantially at an ostium of another body passageway which communicates with the body passageway receiving said prosthesis.

Still further in accordance with the present invention, there is provided an expandable prosthesis for a body passageway comprising a plurality of successive tubular members interconnected together, at least one pair of adjacent alternating tubular members being flexibly connected together with at least one connecting member for allowing said adjacent tubular members to be articulated out of coaxial alignment.

Still further in accordance with the present invention, there is provided an expandable prosthesis for a body passageway comprising at least one tubular member, a side opening being defined laterally in said tubular member of said prosthesis for positioning substantially at an ostium of an other body passageway which communicates with the body passageway receiving said prosthesis, said tubular member having a collapsed diameter for permitting delivery thereof in the body passageway and having at least one expanded diameter upon application from the interior of said tubular member of an outwardly directed force for expanding the body passageway.

Still further in accordance with the present invention, there is provided a method of positioning a prosthesis in a first body passageway at an ostium of a second body passageway communicating with said first body passageway, comprising the steps of providing an expandable prosthesis defining a side opening, inserting said prosthesis into said first body passageway, positioning said prosthesis such that said side opening is substantially opposite said ostium, and expanding said prosthesis against inner walls of said first body passageway with said side opening being located at said ostium.

BRIEF DESCRIPTION OF THE DRAWINGS

Having thus generally described the nature of the invention, reference will now be made to the accompanying drawings, showing by way of illustration a preferred embodiment thereof, and in which:

FIG. 1 is a schematic elevational view of a hexagon ring of a stent in accordance with the present invention, wherein:

FIG. 1A is a schematic representation of the hexagonal pattern of honeycomb and hive;

FIG. 1B is a flattened view of the hexagon ring (ring cut and unfolded) composed of 8 hexagonal elements, with interconnecting members in positions #4 and #8;

FIG. 1C is an elevational view of the hexagon ring with interconnecting members in positions #4 and #8;

FIG. 2 is a schematic elevational view of an inverted hexagon ring in accordance with the present invention, wherein:

FIG. 2A is an hexagonal element;

FIG. 2B is the hexagonal element, stretched to twice its length;

FIG. 2C is the inverted hexagonal element (this represents a modification of the shape of the hexagonal element of FIG. 2A, where the original configuration has been stretched twice its length as in FIG. 2B, and where the left and right sides have been inverted and oriented toward the center of the element);

FIG. 2D is a flattened view of inverted hexagon ring (ring cut and unfolded) composed of 8 inverted hexagonal elements, with interconnecting members in positions #2 and #6;

FIG. 2E is an elevational view of the inverted hexagon ring, with interconnecting members in positions #2 and #6;

FIG. 7A is an elevational view of the stent in an unflexed state;

FIG. 7B is an elevational view of the stent of FIG. 7A having been flexed along the longitudinal axis;

FIGS. 8A and 8B is an elevational view, showing expanded and contracted states, the effect of the interconnecting members on limiting longitudinal expansion or contraction during radial expansion and deployment being also depicted;

FIGS. 9A to 9C is an elevational view, showing that various stent lengths are possible by repeating the alternate ring pattern;

FIG. 10A is a perspective representation of a stent mounted and crimped on a delivery catheter, advanced within a blood vessel (cut longitudinally) at the level of a target segment, the blood vessel, depicting a suboptimal result left after conventional balloon angioplasty, with a residual stenosis limiting blood flow;

FIG. 10B shows a passive radial expansion of the stent of FIG. 10A generated by the radial forces of an inflating balloon of the delivery catheter;

FIG. 10C shows the balloon of FIG. 10B deflated, leaving the stent expanded against the vessel wall;

FIG. 10D shows the delivery catheter of FIGS. 10A to 10C pulled back, with the stent expanded and correction of suboptimal result;

DESCRIPTION OF THE PREFERRED EMBODIMENTS

Figure 1:
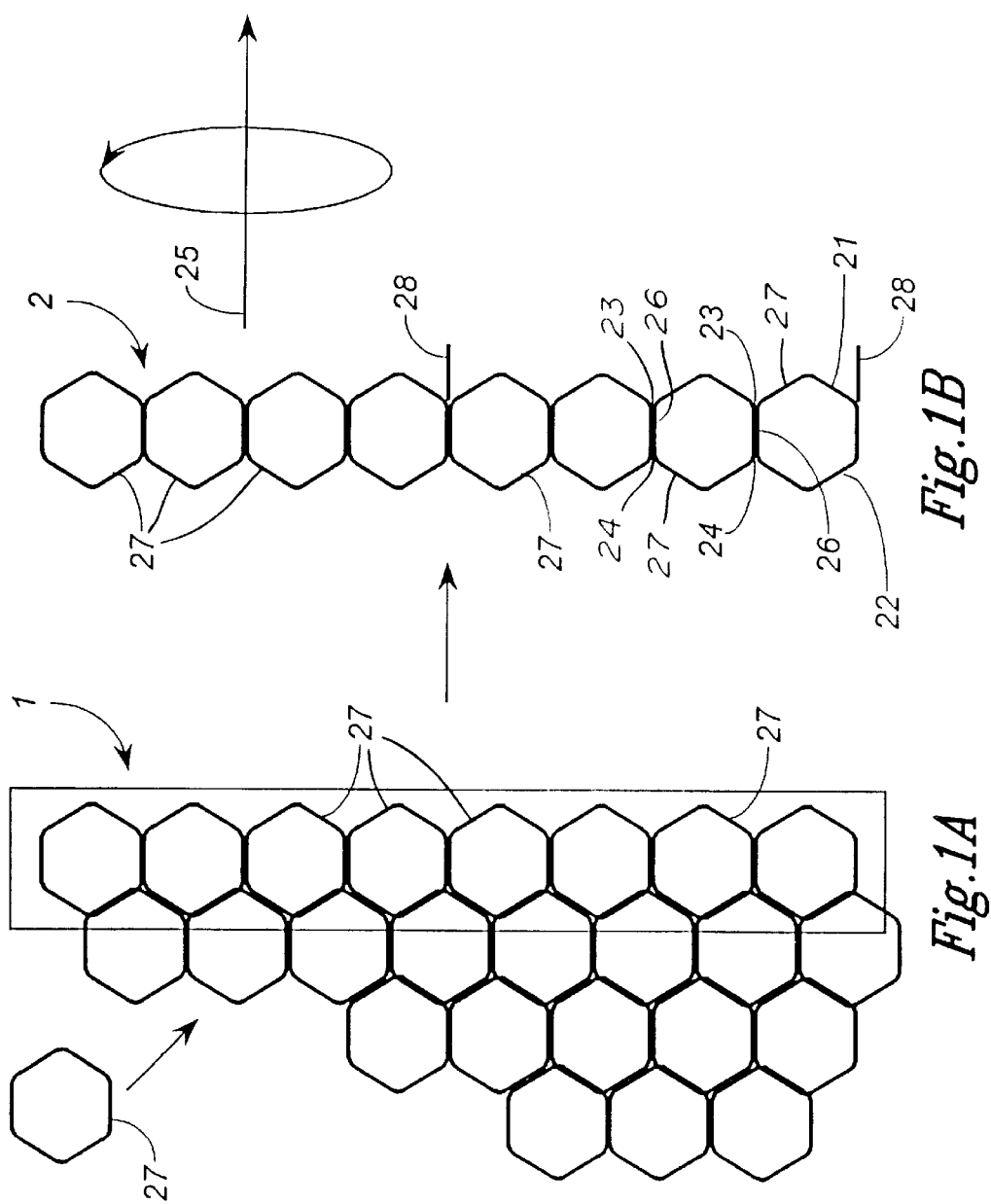

One of the unique concepts of the stent of the present invention is based on the honeycomb and the hive, a hexagonal pattern 1 found in nature that provides a relatively strong scaffolding structure despite its thin walls and the relatively low density of material used in its elaboration (FIG. 1A).

Figure 2:
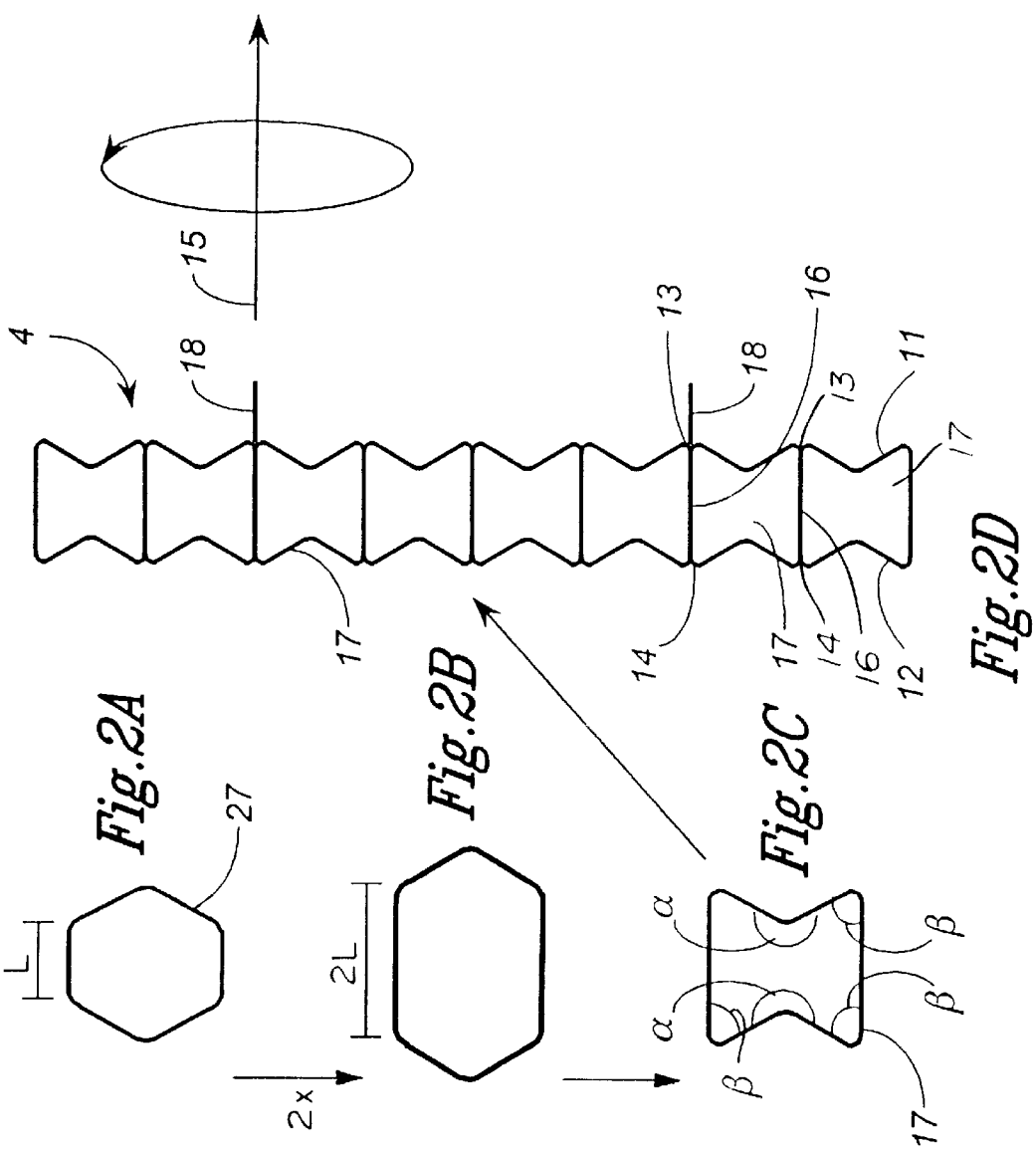

A chain of eight (8) honeycomb-like hexagonal components 27 in the form of a strip 2 (FIG. 1B) is used to form the first type of ring element 3 (called "hexagon ring") by joining both free ends of the strip (FIG. 1C) Similarly, a chain 4 of eight (8) "inverted"hexagonal components 17 is used to form a second type of ring element 15 (called "inverted hexagon ring"), as seen in FIGS. 2D and 2E. The inverted hexagonal component 17 represents a modification of the shape of the hexagonal component 27 (FIG. 2A), where the original configuration has been stretched twice its length (FIG. 2B), and where the left and right sides have been inverted and oriented toward the center of the element (FIG. 2C). Two of the internal angles are thus greater than 180° (see angles α in FIG. 2C).

As shown in FIG. 2D, an inverted hexagonal ring element 5 shown in opened out form 4, is constituted by two zigzag bands 11 and 12 which have the same shape and are aligned so that the troughs 13 of band 11 are aligned on a line parallel with the axis 15 with peaks 14 of the band 12. Troughs 13 are joined to peaks 14 each by connector 16, thereby forming the series of inverted hexagon shapes 17. The internal angle α is greater than 180°, whilst the internal angle β is less than 90°.

Similarly, as shown in FIG. 1B, an unfolded ring element 2 of hexagonal components 27 is formed of a pair of bands 21, 22 having respective aligned peaks 23 and troughs 24, aligned on a line parallel with the axis 25 of the ring element 3. The peaks 23 are each joined to troughs 24 by connectors 26 to form hexagon component 27.

Between adjacent inverted hexagon ring element 5 and hexagon ring element 3 are a pair of interconnecting links 18. These are arranged so as to be aligned each with a connector 16 and so that the two links 18 are diametrically opposed in the ring element. Joining the next pair of hexagon ring element 3 and inverted hexagon ring element 5 is a further pair of links 28, again each of which is aligned with a connector 26, with the two links 28 being diametrically opposed in the ring element. The diameter joining the pair of links i8 is at an angle of 90° to the diameter joining the pair of links 28.

Figure 3:
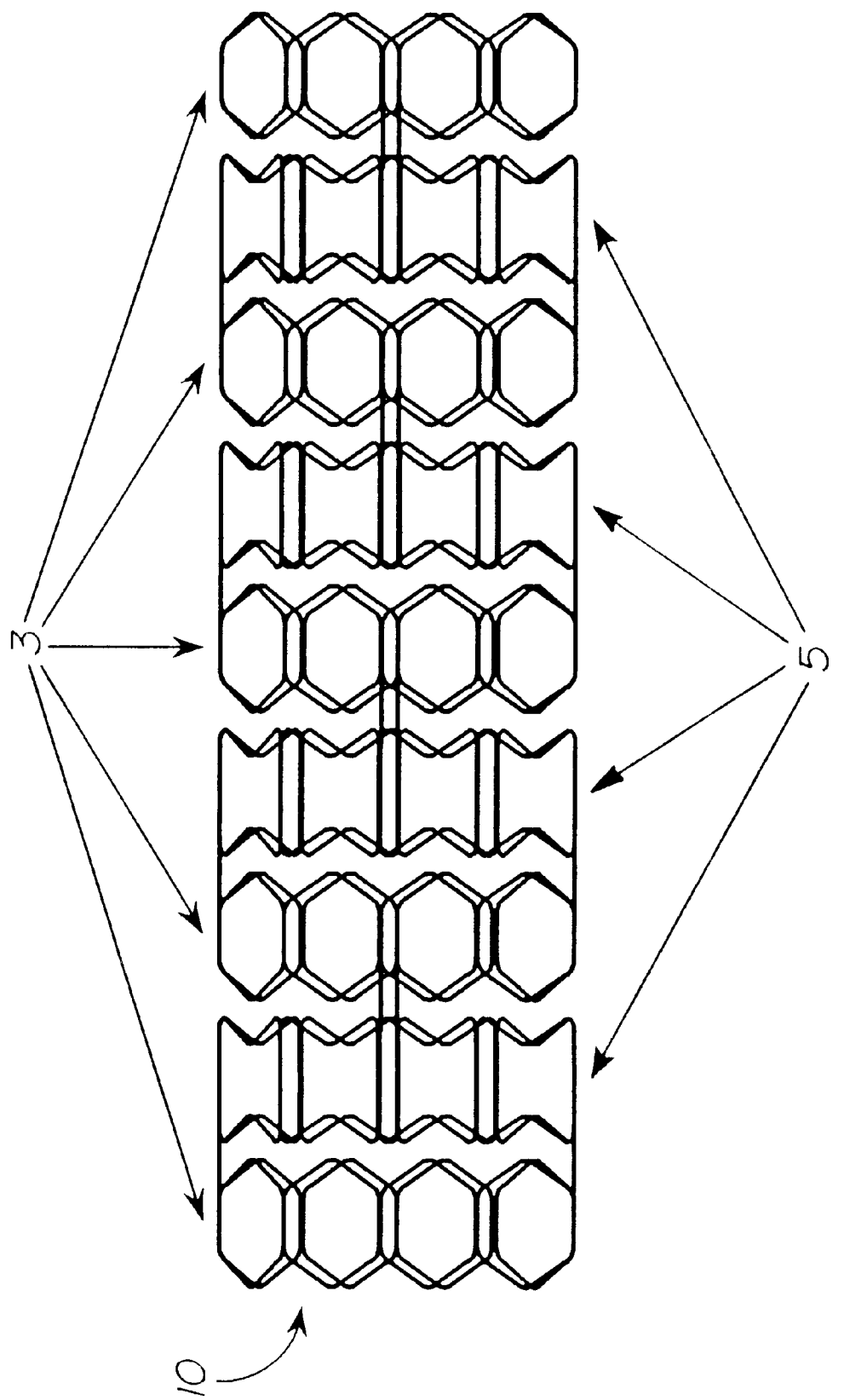
FIG. 3 is an elevational view of the stent, composed of adjacent hexagon rings and inverted hexagon rings, with an alternate configuration over the longitudinal axis of the stent.
Figure 4:
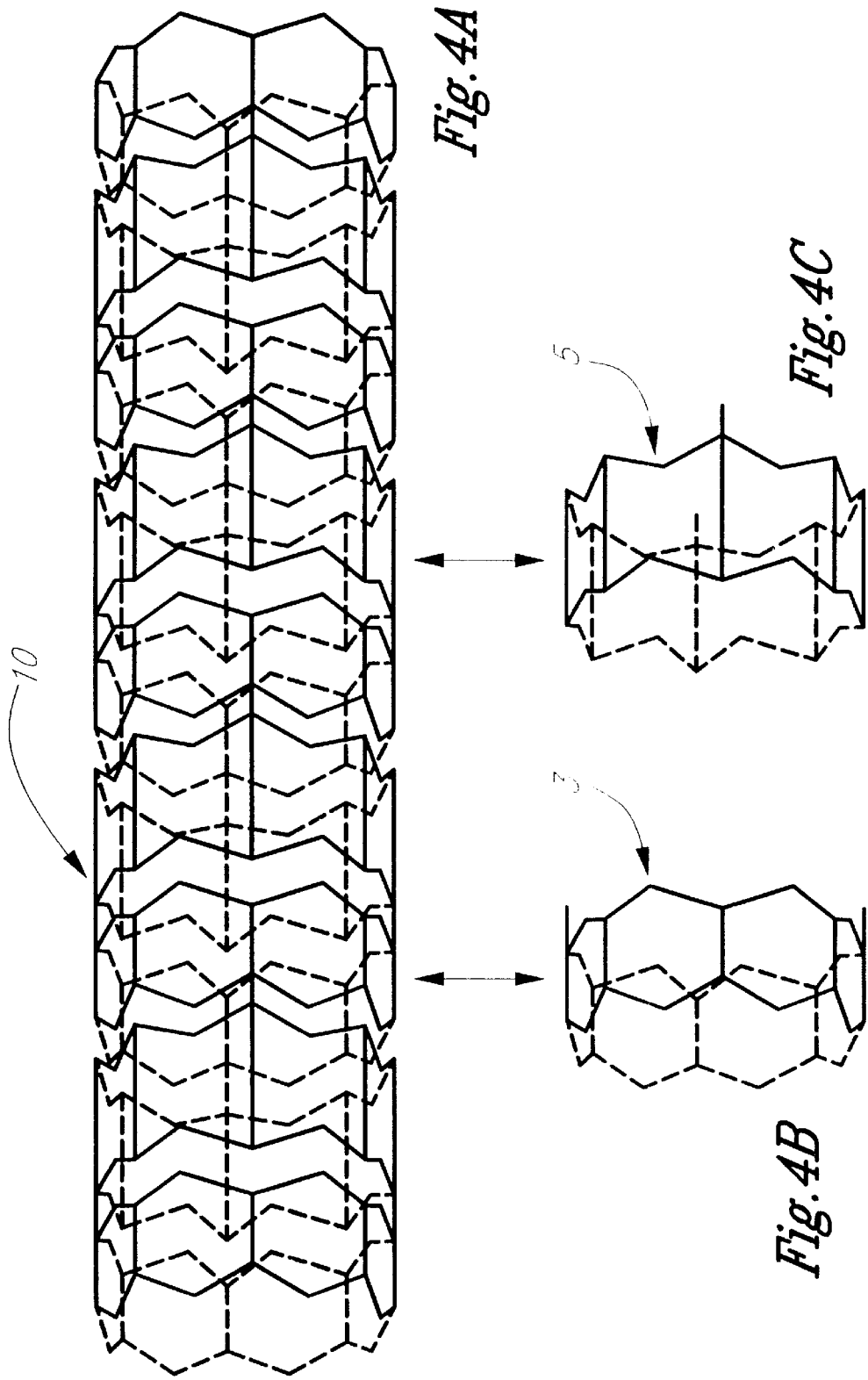
FIGS. 4A, 4B, and 4C is a schematic representation of the stent in perspective (3-dimensional) view, showing also the respective structural aspect of single hexagon and inverted hexagon rings (duplicated)
Figure 5:
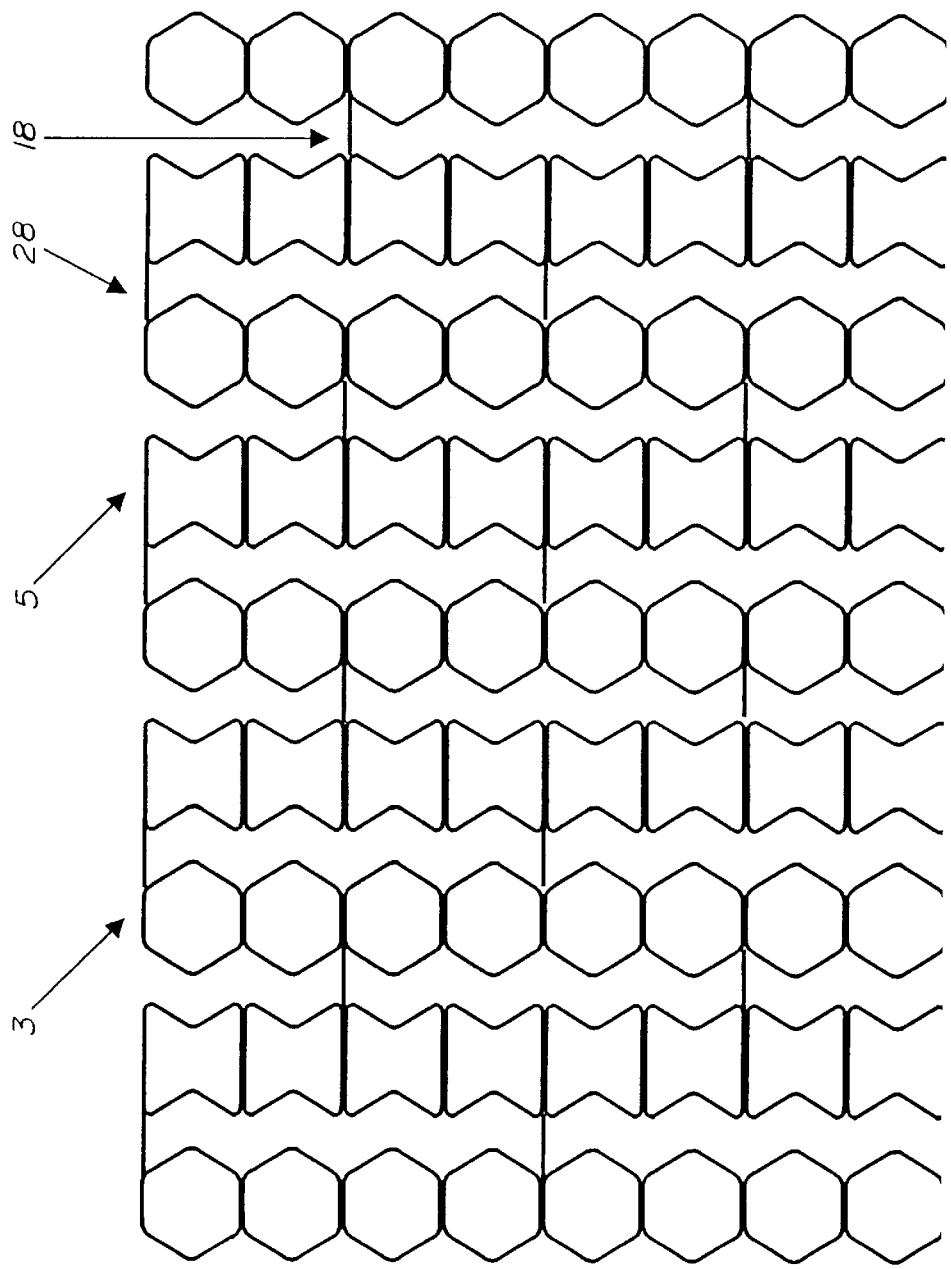
FIG. 5 is a flattened view of stent (cut longitudinally and unfolded), showing the repetitive pattern of the meshwork, generated by the alternate configuration of hexagon rings and inverted hexagon rings, and providing adequate vessel wall coverage, the alternate disposition of interconnecting members being also shown.

A stent 10 is composed of a plurality of adjacent hexagon ring elements 3 and inverted hexagon ring elements 5, with an alternate configuration over the longitudinal axis of the stent 10 (FIGS. 3 and 4), in order to reduce gaps between adjacent ring elements 3,5 and to provide an adequate vessel wall coverage and a strong scaffolding structure (FIG. 5).

Figure 6:
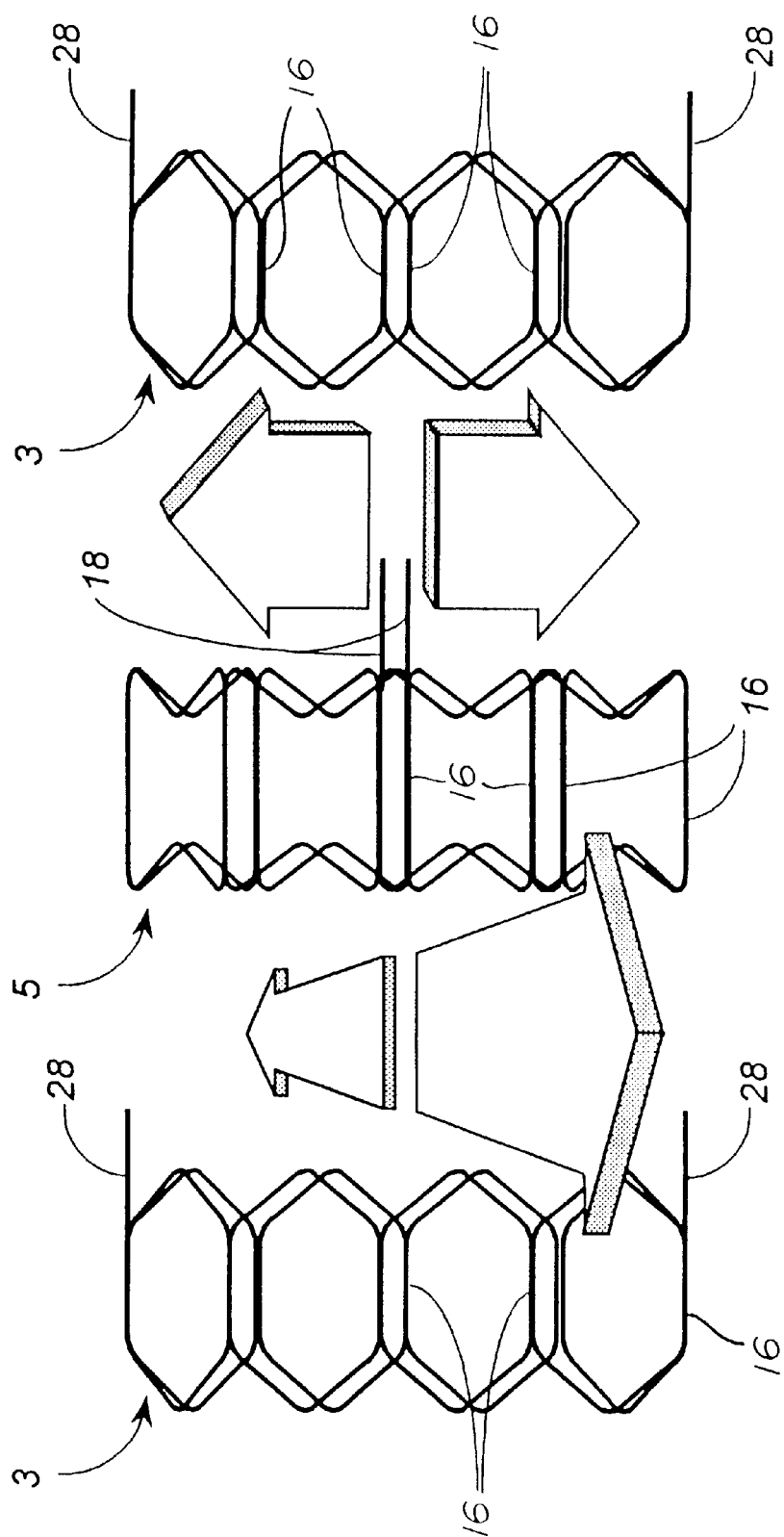
FIG. 6 is a schematic representation of the relative flexibility in perpendicular planes, provided by the particular design of the present stent.

A set of two interconnecting links 18 or 28 is used to join a ring element 3,5 to the adjacent ring element 5,3. The interconnecting links 18,28 are positioned at every four (4) hexagon shapes, i.e. in a diametrically opposed manner. This provides two interconnecting links in one plane for connection to the adjacent ring. For instance, on the hexagon ring element 3, the interconnecting links 28 are placed in positions #4 and #8 (FIG. 1B), while on the inverted hexagon ring element 5, the interconnecting links 18 are placed in positions #2 and #6 (FIG. 2D). This results in a 90° rotation (or offset) between each set of interconnecting members, which provides a relative flexibility in perpendicular planes, along the longitudinal axis of the stent (FIGS. 6, 7A and 7B), in either the contracted or expanded states. The interconnecting links 18,28 since they are aligned with connectors 16 in adjacent ring elements 3,5, also ensure that longitudinal expansion or contraction is limited during radial expansion and deployment, which allows a predictable stent positioning (FIG. 8). possible, in order to accommodate specific clinical indications (FIG. 9).

A delivery catheter 30 on which the stent 10 is mounted and crimped can be essentially the same as a conventional balloon catheter used for angioplasty procedures, as far as the balloon material of a balloon 32 thereof is suitable for stent deployment (FIGS. 10A to 10D) within a blood vessel 34.

Directional Stent for Anatomical Bifurcations

Figure 11A:
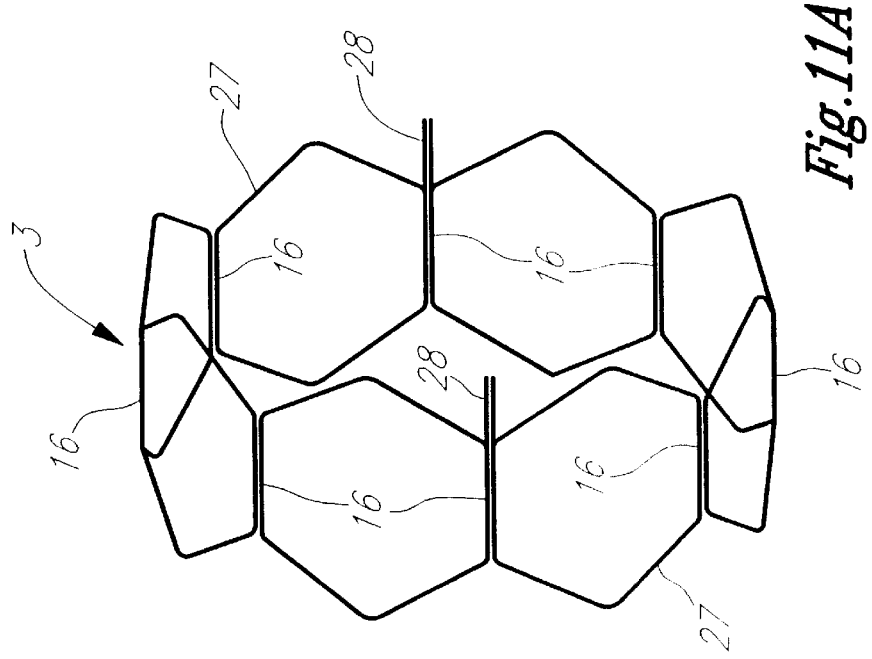
FIGS. 11A and 11B are perspective representations of a hexagonal ring and n inverted hexagonal ring, displayed separately, with the interconnecting members being also shown.
Figure 11B:
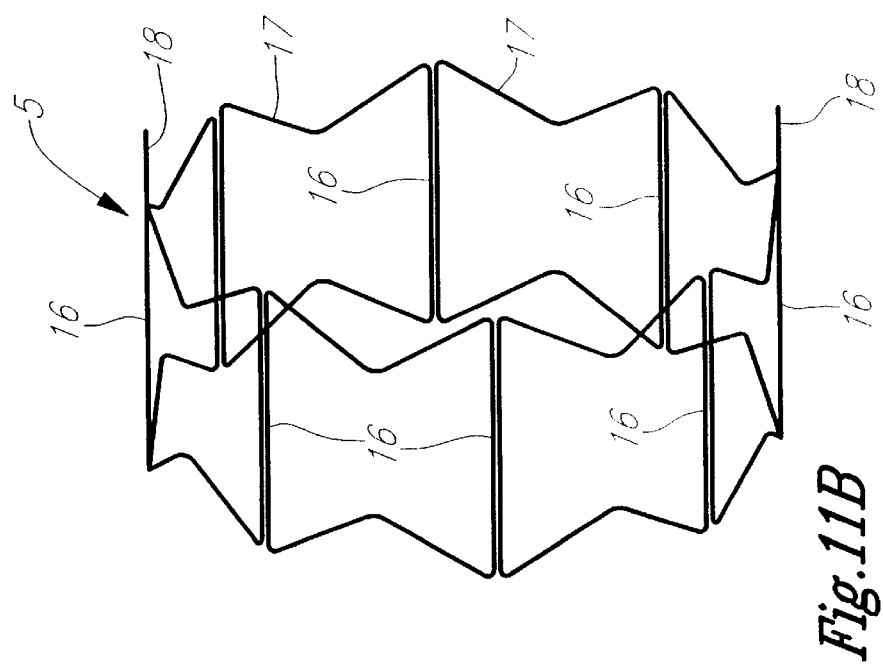
Figure 12:
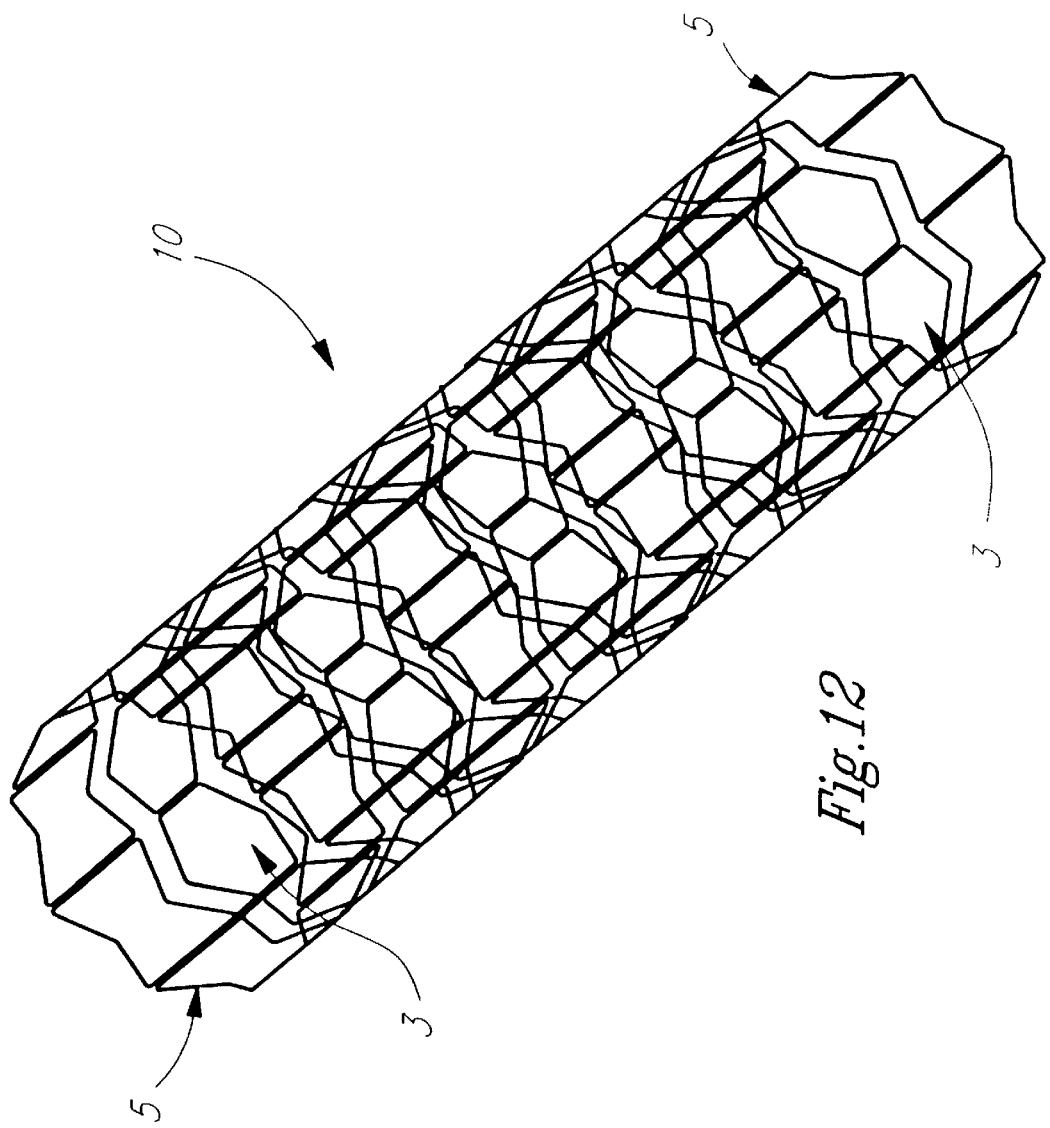
FIG. 12 is a perspective representation of the monotubular stent.
Figure 13:
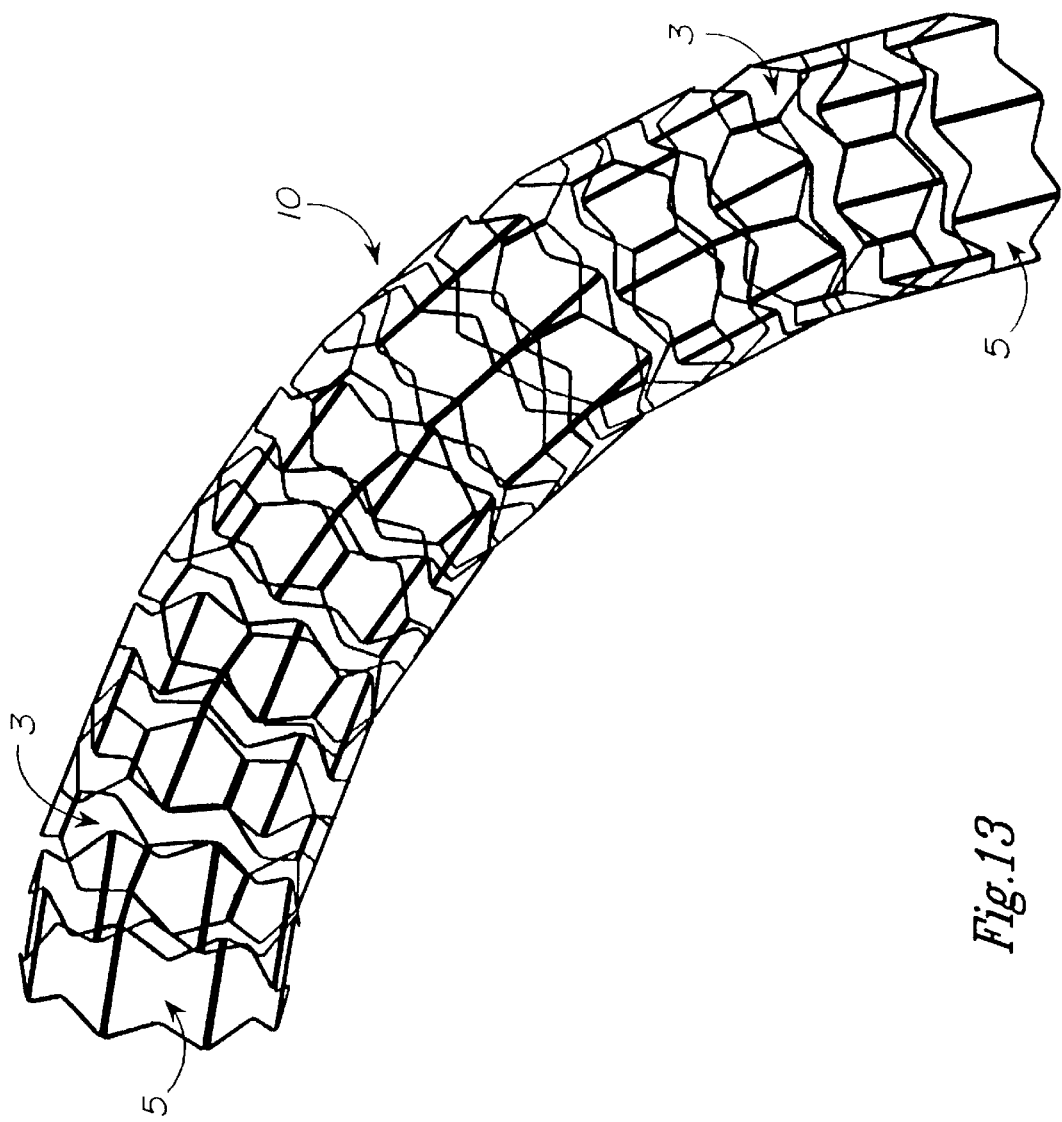
FIG. 13 is a perspective representation showing the flexibility of the stent, resulting from the particular disposition of the interconnecting members.

With reference to FIGS. 11 to 13, the above basic stent 10 is made of a chain of eight (8) honeycomb-like hexagonal elements 27 is used to form the first type of ring 3 (called "hexagon ring"). A chain of eight (8) "inverted"hexagonal elements 17 is used to form the second type of ring 5 (called "inverted hexagon ring"), both rings 3 and 5 being shown in FIG. 11. The inverted hexagonal element 17 represents a modification of the shape of the hexagonal element 27, where the original configuration has been stretched twice its length, and where the left and right sides have been inverted and oriented toward the center of the element.

The stent 10 is composed of a plurality of adjacent hexagon rings 3 and inverted hexagon rings 5, with an alternate configuration over the longitudinal axis of the stent, in order to reduce gaps between rings 3,5 and to provide an adequate vessel wall coverage and a strong scaffolding structure (FIG. 12).

A set of two interconnecting members 18 or 28 is used to join a ring 3,5 to the adjacent one 5,3. The interconnecting members are positioned at every four (4) elements, which provides two interconnecting members in one plane for connection to the adjacent ring. The 90° rotation between each set of interconnecting members provides a relative flexibility in perpendicular planes, along the longitudinal axis of the stent (FIG. 13) in either the contracted or the expanded state. The interconnecting members 18,28 also insure that longitudinal expansion or contraction is limited during radial expansion and deployment, which allows a predictable stent positioning.

Now referring generally to FIGS. 4 to 25, the present invention also relates to the concept of "directional stenting", where a lateral opening 42 is created in the middle of the body of the stent 10 thereby resulting in a variant stent 40, so that this lateral opening 42 can be steered and aligned with the ostium of a bifurcation or a side branch of a blood vessel, using a specific delivery system, as detailed hereinbelow.

Stent with Lateral Opening

Figure 14:
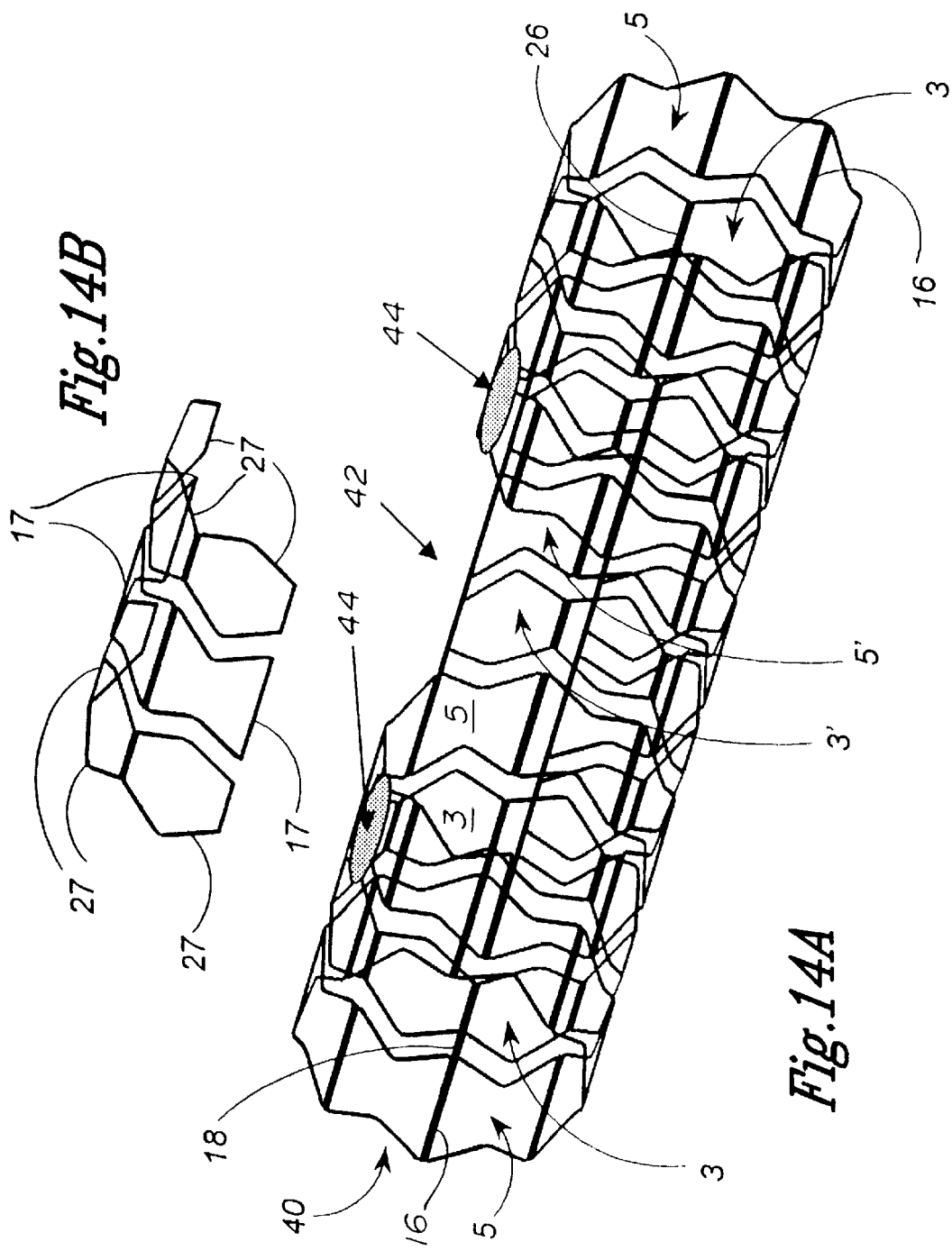
FIGS. 14A and 14B is a perspective representation of another stent provided with a lateral opening (displayed on top of the stent body) also in accordance with the present invention, and further showing how this opening is created and also the provision of radiopaque markers.

On three or more consecutive rings 3,5 (either hexagonal 3 or inverted hexagonal 5 rings) located in the middle portion of the stent body 10, the lateral opening 42 is created by removing 3 contiguous hexagon components 17,27 along the cross-sectional axis of each ring 5,3, leaving three opened rings 3',5',3' each composed of five hexagon elements 17,27. Thus, the middle portion of the stent body 40 is composed of three or more opened rings, which constitutes the lateral opening 42. Interconnecting members 18,28 are arranged in order to maintain integrity and relative flexibility. Radiopaque markers 44 are. placed on each side of the lateral opening 42, in order to optimize stent placement and alignment under fluoroscopic guidance (FIG. 14).

Delivery System

Figure 15:
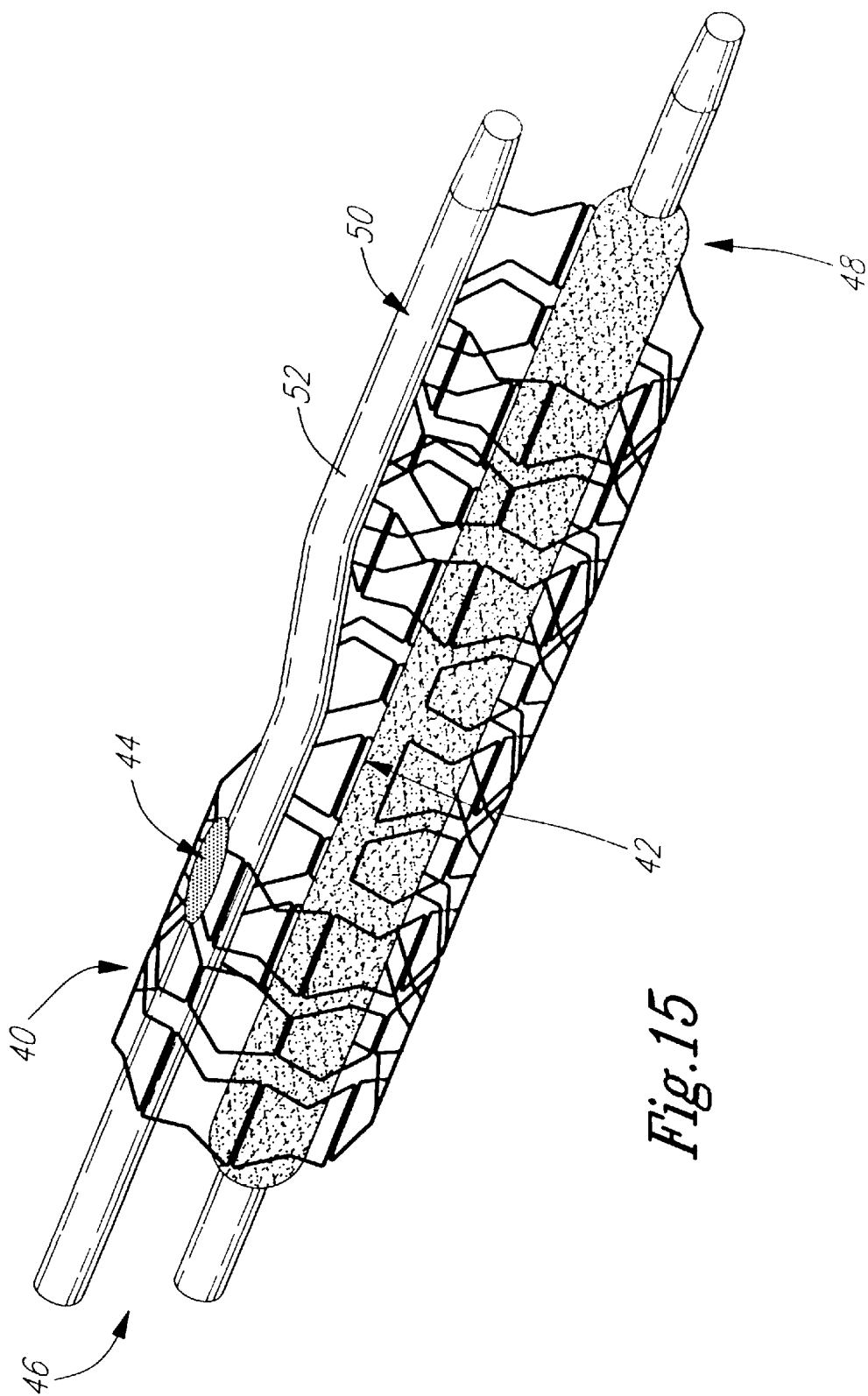
FIG. 15 is a perspective representation of the components of a delivery system for the stent of FIG. 14.

The delivery system 46 is composed of a) a balloon catheter 48 and b) a steering catheter 50. The balloon catheter 48 is placed inside the stent 40, over its longitudinal axis. The steering catheter 50 is placed also inside the stent 40, alongside the balloon catheter 48, but with its distal tip 52 exiting through the lateral opening 42. The balloon catheter 48 is used to expand the stent 40 after adequate positioning. The steering catheter 50 is used to engage the side branch of the blood vessel and align the lateral opening 42 with the ostium of the side branch (FIG. 15).

Figure 16:
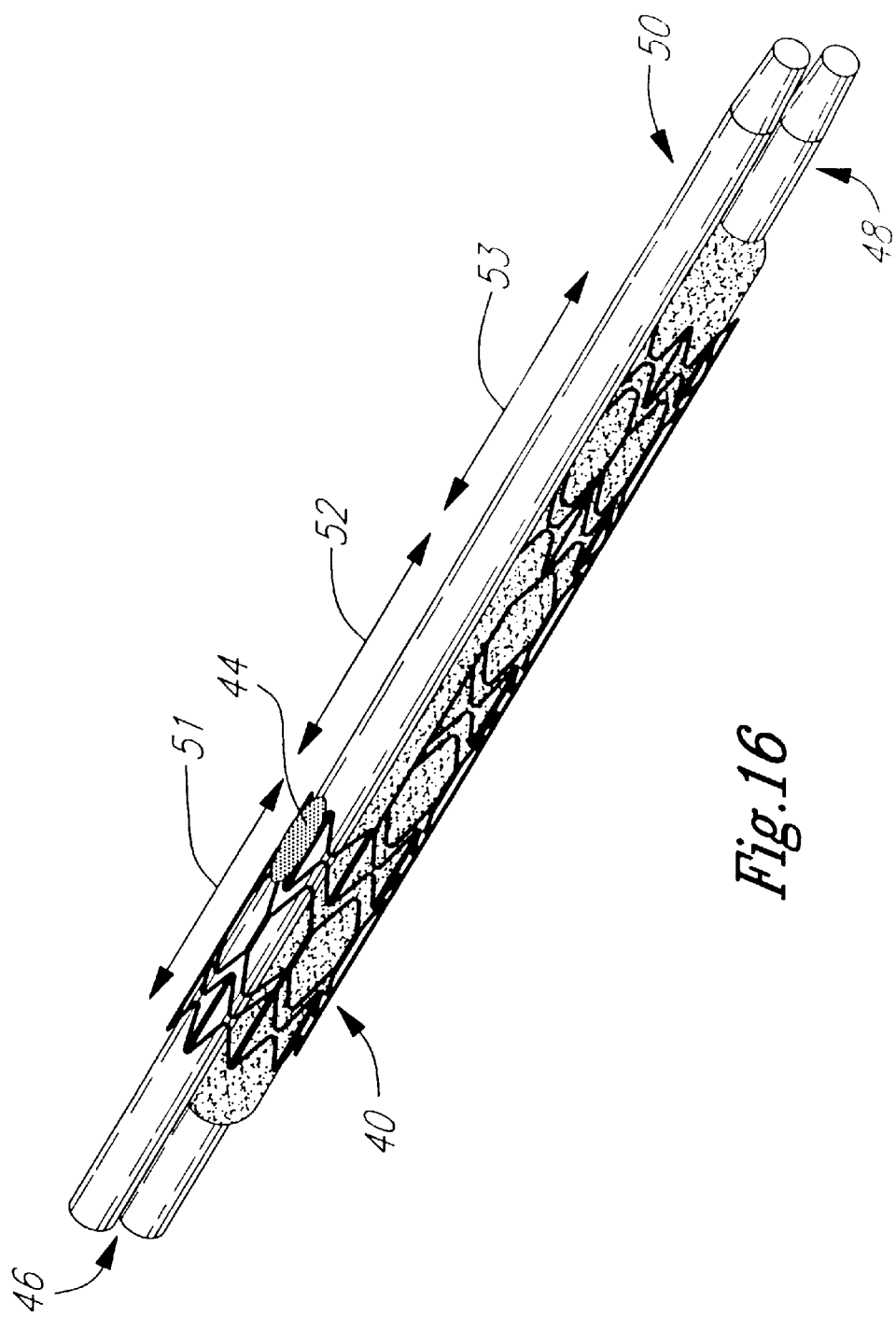
FIG. 16 is a perspective representation of the stent crimped on the delivery system.

For intraluminal delivery, the proximal part 51 of the stent 40 is crimped on the body of the steering catheter 50 and on the body of the balloon catheter 48. The middle portion 52 of the stent 40 corresponding to the area of the lateral opening 42 is crimped only on the body of the balloon catheter 48. The distal part 53 of the stent 40 i s also crimped only on the body of the balloon catheter 48 (FIG. 16).

Deployment Technique

Figure 17:
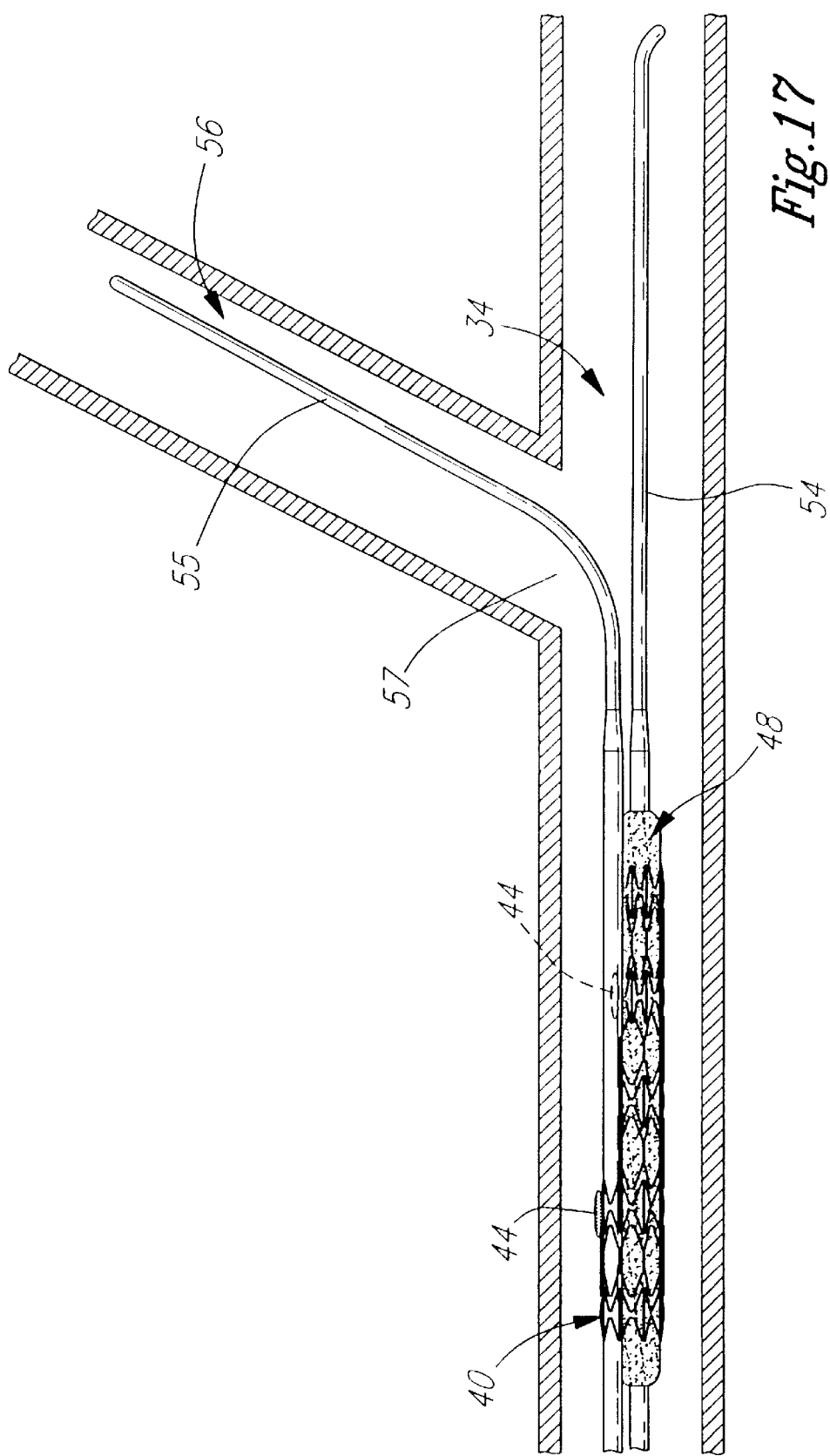
FIG. 17 is a schematic longitudinal cross-sectional view showing the delivery system proximal to a target site.
Figure 18:
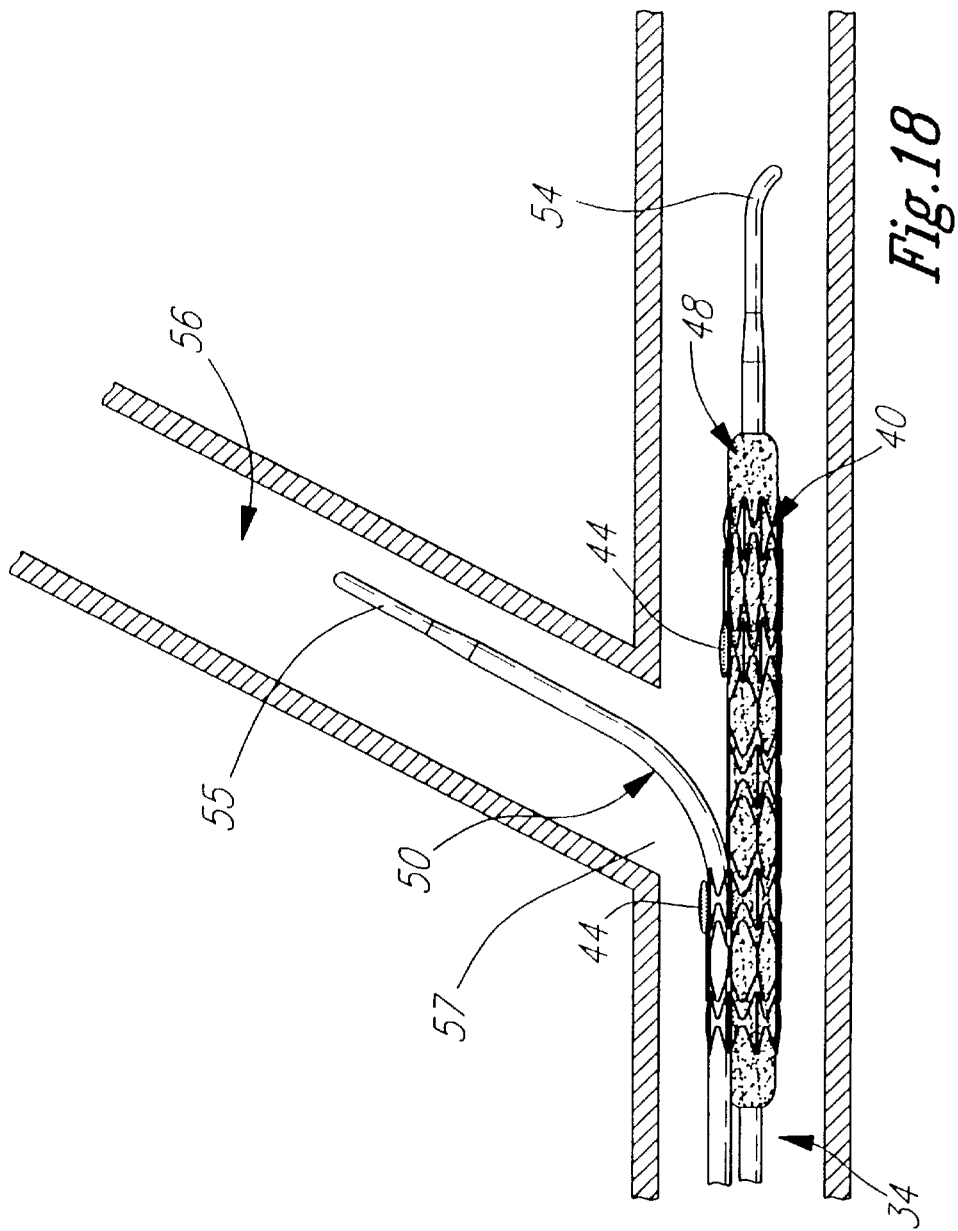
FIG. 18 is a schematic longitudinal cross-sectional view showing placement of the delivery system at the target site.
Figure 19:
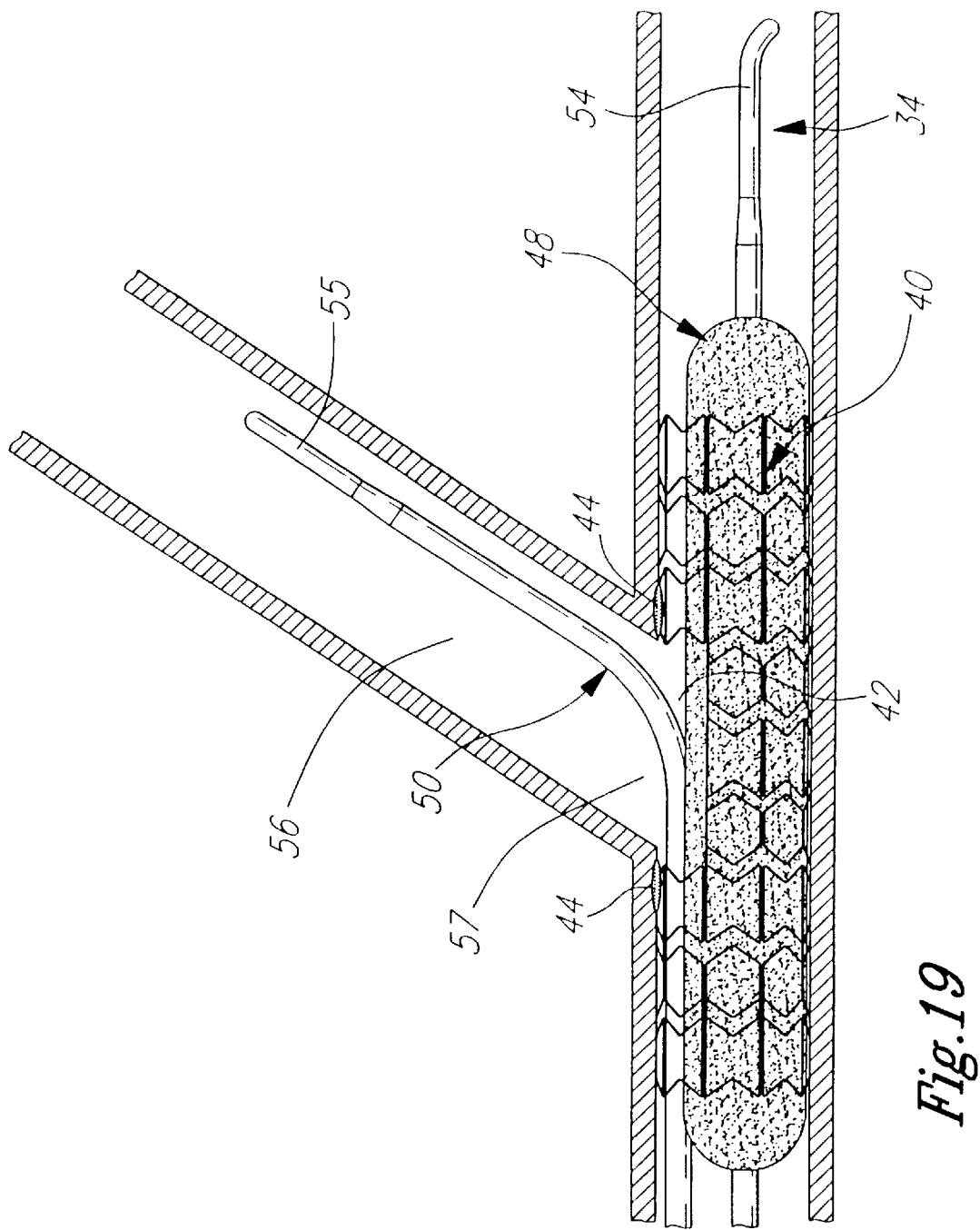
FIG. 19 is a schematic longitudinal cross-sectional view showing stent deployment by the balloon catheter.
Figure 20:
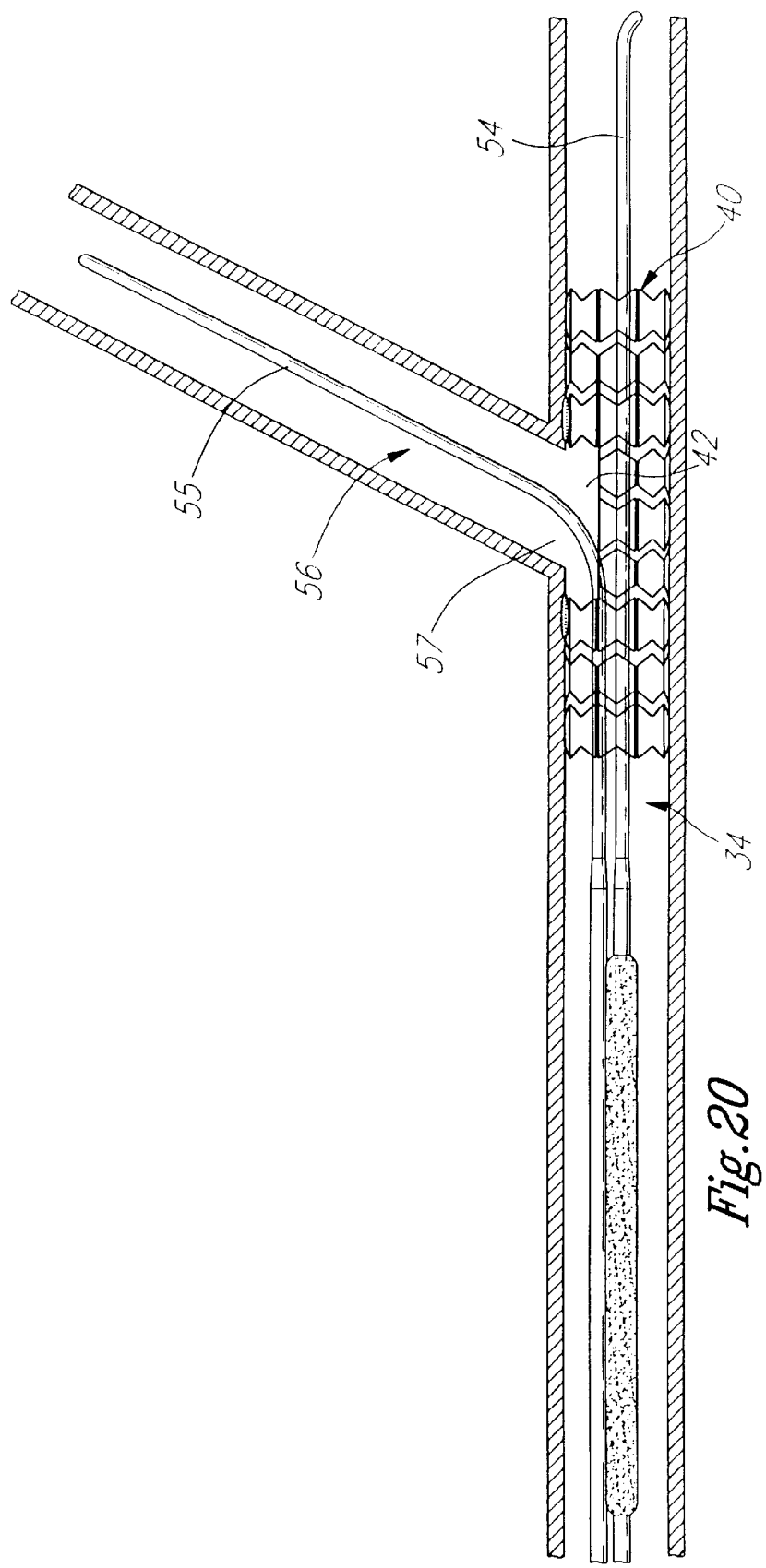
FIG. 20 is a schematic longitudinal cross-sectional view showing the stent deployed and the delivery system pulled back.
Figure 21:
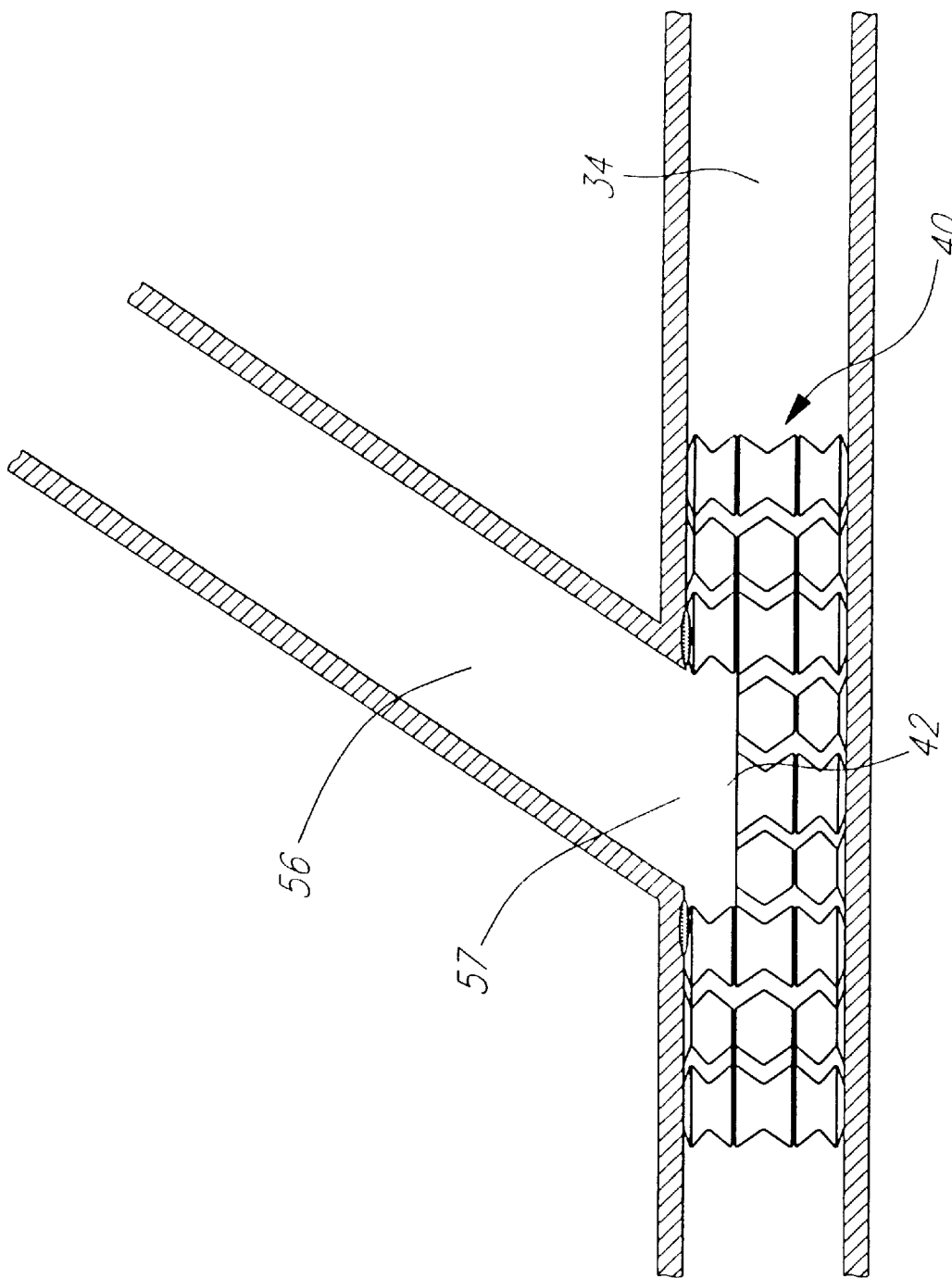
FIG. 21 is a schematic longitudinal cross-sectional view showing final placement of stent and guide wires pulled back.

Under fluoroscopic guidance, a 0.014" angioplasty guide wire 54 is advanced and positioned into the principal passageway 34. A second guide wire 55 is positioned into the secondary passageway 56 to be protected. The delivery system 46 is then mounted on the two guide wires 54 and 55 and advanced at the level of the target site, with special care to mount the balloon catheter 48 on the guide wire 54 lying into the principal passageway 34 (FIG. 17). As the delivery system 46 approaches the side branch 56, predisposition of the guide wires 54,55 serve to orientate the tip of the steering catheter 50 into the secondary passageway 56 and the balloon catheter 48 into the principal passageway 34. Under fluoroscopic guidance, optimal alignment of the lateral opening 42 of the stent 40 with the ostium 57 of the secondary passageway 56 is achieved using the radiopaque markers 44 on the body of the stent 40 and contrast injection (FIG. 18). Once placement is satisfactory, the stent 40 is expanded by the radial forces of the inflating balloon catheter 48, which results in stent 40 apposition against the wall of the principal passageway 34 (FIG. 19). Then, the balloon catheter 48 is deflated, collapsed and pulled back outside the stent 40. Afterwards, the steering catheter 50 is pulled back outside the lateral opening 42 and outside the stent 40, leaving the deployed stent 40 with the two guide wires 54,55 in their respective passageways (FIG. 20). To further improve wall apposition of the stent 40, additional inflations with larger balloon catheters or with high-pressure balloon catheters can be performed. When the result is satisfactory, the guide wires 54,55 are then removed from their respective passageways (FIG. 21).

Technical Variations a) Guide Wire Entanglement

Figure 22:
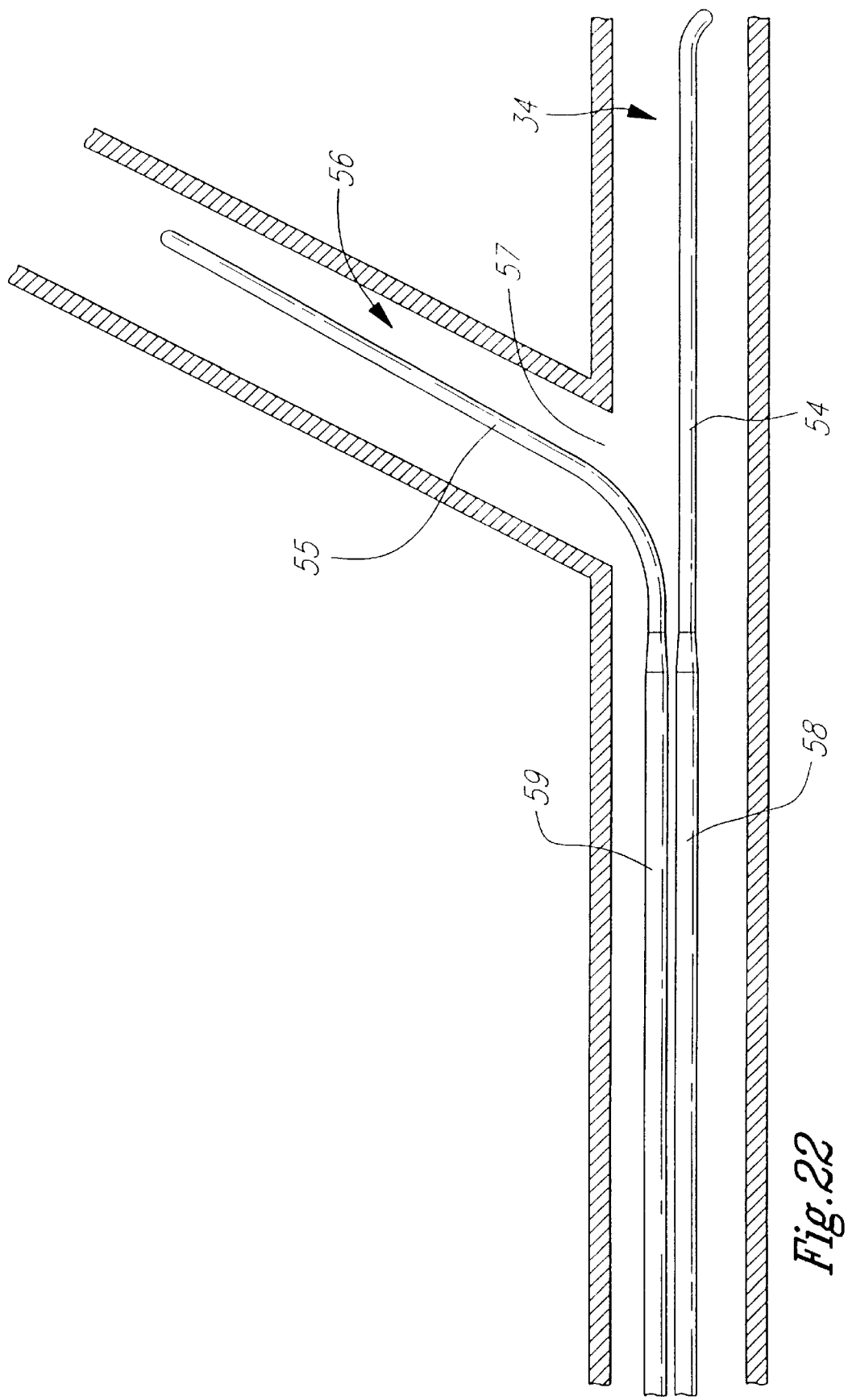
FIG. 22 is a schematic longitudinal cross-sectional, view showing probing catheters at the level of bifurcation.
Figure 23:
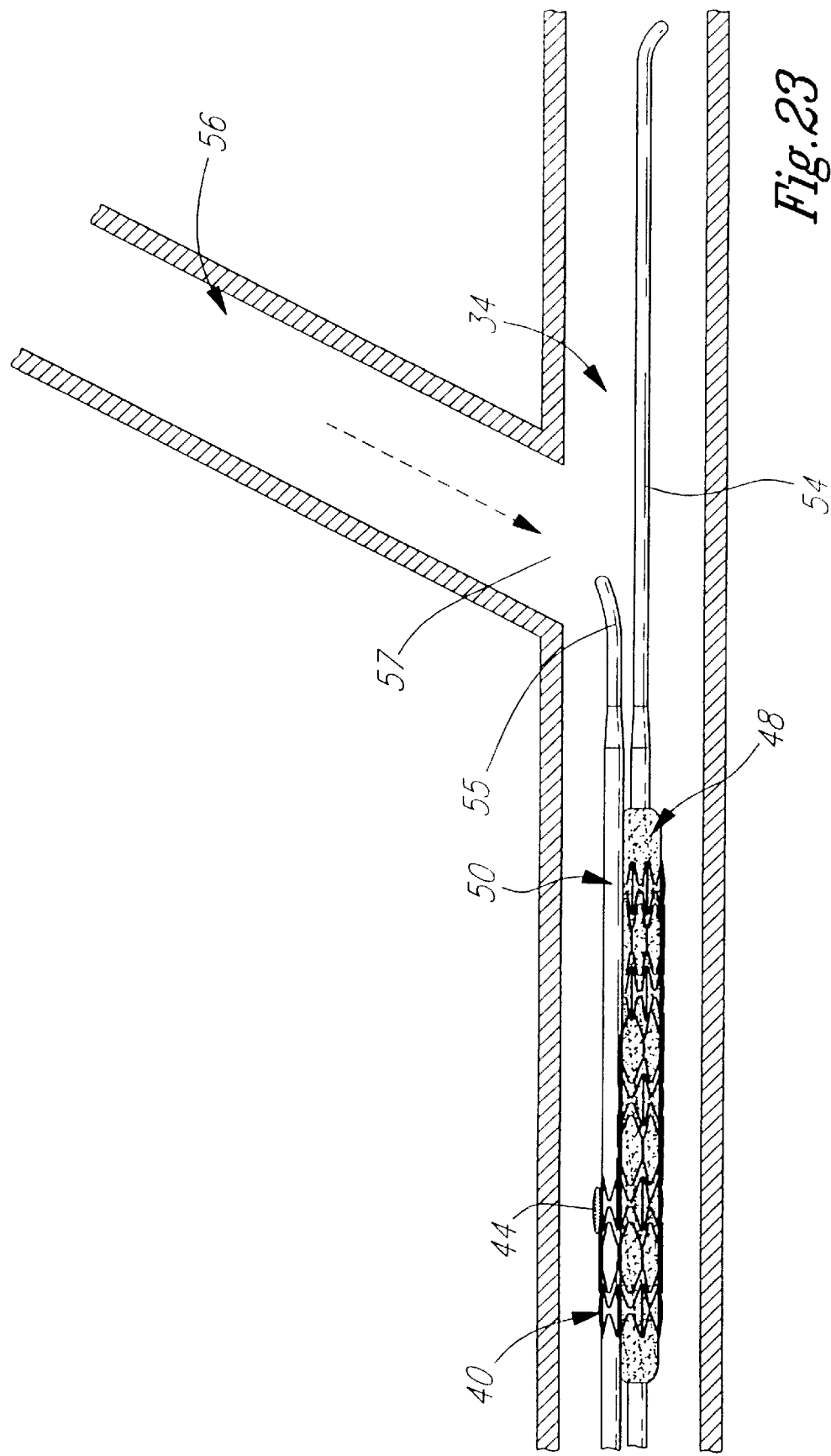
FIG. 23 is a schematic longitudinal cross-sectional, view showing a method for unraveling guide wires when the delivery system is already engaged into the principal passageway.
Figure 24:
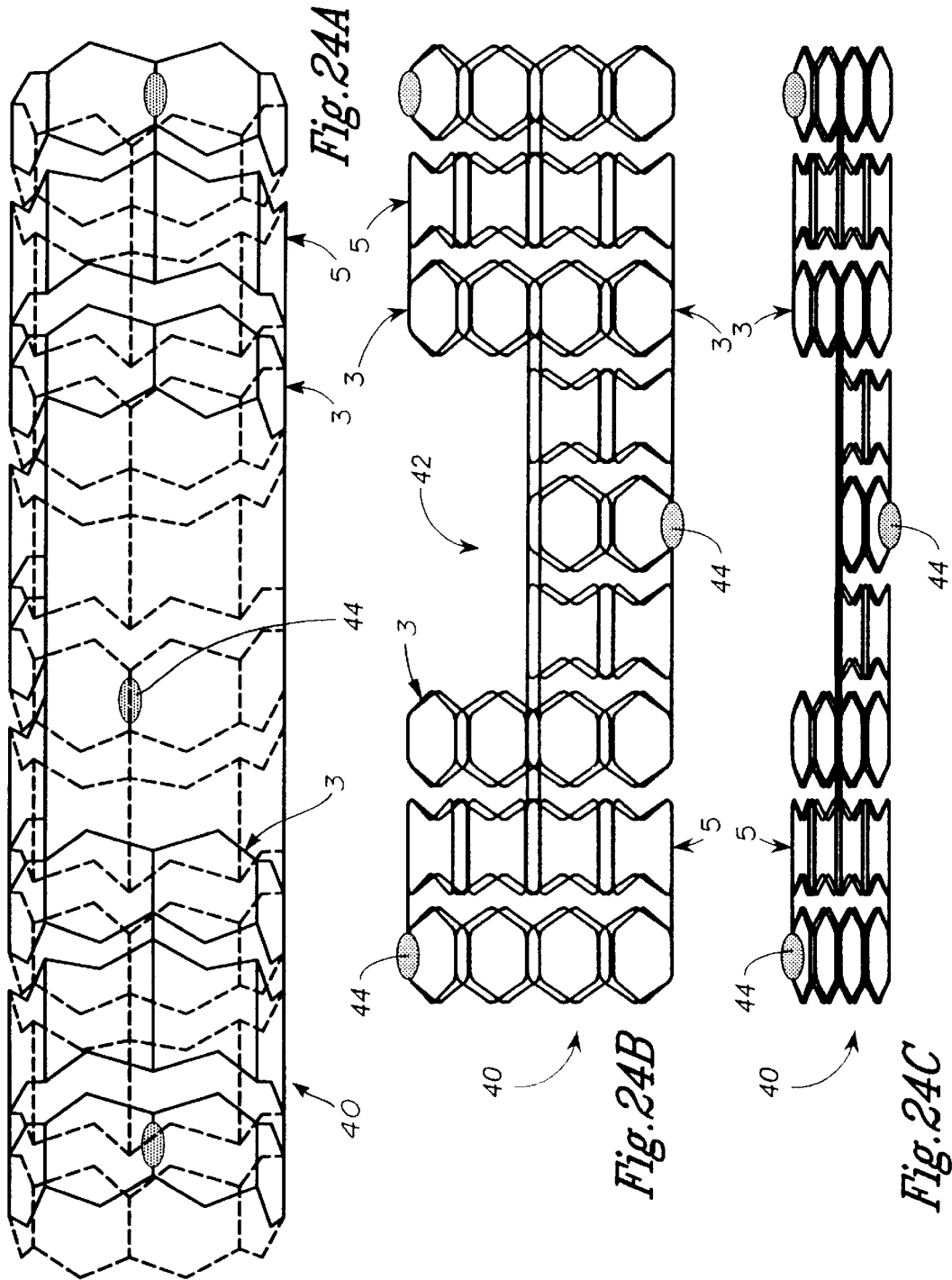
FIGS. 24A to 24C is a perspective (deployed) and elevational (deployed and collapsed) views of the stent with lateral opening and radiopaque markers.

Guide wire entanglement has the potential to lead to technical problems while advancing and positioning the delivery system 46. In order to avoid such technical problems or whenever this situation is suspected, the following procedure can be performed:

before mounting the delivery system 46 on the two guide wires 54,55, wire entanglement can be ruled out by mounting simultaneously two independent "probing" catheters 58 and 59 on the two guide wires 54 and 55 and advancing them at the target site. Probing catheters, which are commercially available, are similar in shape and design to the steering catheter 50 of the delivery system 46. This technique will help to unravel any entanglement and allow testing of catheter movement up to the target site (FIG. 22).

if the delivery system 46 is already engaged into the principal passageway 34 and progression is impeded by guide wire entanglement, the delivery system 46 can also be pulled back over 2 or 3 cm. Then, the guide wire 55 lying into the secondary passageway 56 is pulled back completely into the inner lumen of the steering catheter 50. This will eliminate any entanglement between the two guide wires 54 and 55 (FIG. 23). As this point, the guide wire 55 can be readvanced and repositioned into the secondary passageway 56 and the delivery system 46 can then be advanced safely at the target site.

b) Stenting in the Secondary Passageway

Figure 25:
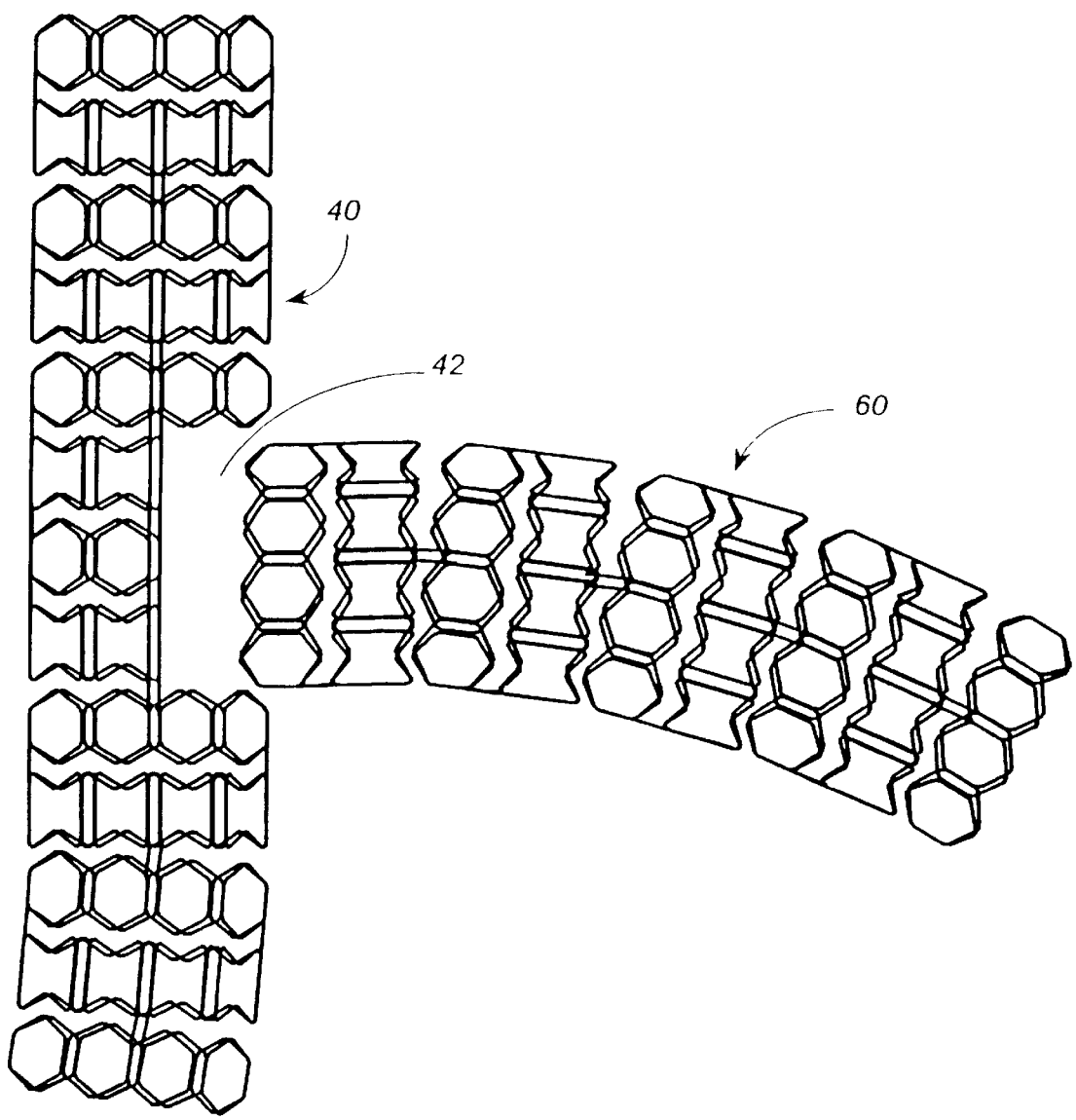
FIG. 25 is a schematic elevational view of a secondary stent in side branch extending opposite the lateral opening of the primary stent of FIGS. 14 to 24.

In the situation where a significant narrowing is present in the secondary passageway 56 and intervention is planned, stenting (if needed) should be performed first in the secondary passageway 56. Otherwise, attempts at advancing a monotubular stent 60 (crimped on a balloon catheter 48) across the lateral opening 42 of a deployed stent 50 in the main passageway 34 may result in stent mesh entrapment, necessitating emergency bypass surgery (FIG. 25).

Advantages of the hexagonal cell design

The unique concept of this stent is based on the honeycomb and the hive, a hexagonal cellular pattern found in nature that provides a relatively strong scaffolding structure despite its thin walls and the relatively low density of material used in its elaboration.

The alternating configuration of hexagonal (with convex lateral sides) and inverted hexagonal cells (with concave lateral sides) over the longitudinal axis of the stent provides a unique geometrical pattern, leading to a) optimal wall coverage after stent deployment and b) limitation of longitudinal shortening during radial expansion.

The hexagonal cellular pattern allows optimal radial strength of the stent after radial expansion.

The hexagonal cellular pattern allows to create a lateral opening in the middle of the stent body by deletion of one or more hexagonal cells while maintaining the structural integrity of the stent, so that lateral opening can be steered and aligned with the ostium of a bifurcation or a side branch, using a specific delivery system (defined as the concept of "directional stenting").

The unique hexagonal cellular pattern provides optimal geometry for uniform wall irradiation in the situation where stents are used to deliver local radiotherapy.

I claim:

1. An expandable prosthesis for a body passageway comprising a plurality of first and second ring-shaped members having ends of complementary shape, at least some of said first members alternating with said second members in a tubular configuration along a longitudinal axis, pairs of adjacent ring-shaped members being interconnected, at least one of said pairs of adjacent alternating first and second members being flexibly connected together with at least one connecting member for allowing said adjacent first and second members to be articulated out of coaxial alignment, said first and second members each having a collapsed diameter for permitting delivery thereof in the body passageway and having at least one expanded diameter upon application from the interior of said first and second members of an outwardly directed force for expanding the body passageway, wherein said first ring-shaped members are constituted of successive interconnected first elements of polygonal shape when expanded and said second ring-shaped elements are constituted of successive interconnected second elements of inverted polygonal shape, wherein peaks and valleys of adjacent first and second elements are disposed substantially axially opposite from each other in an at least partly nested relationship.

2. A prosthesis as defined in claim 1, wherein said first elements are shaped as hexagons, whereas said second element are shaped as inverted hexagons, and wherein throughout said prosthesis said first and second ring-shaped elements are disposed in a an alternating relationship.

3. A prosthesis as defined in claim 2, wherein there are at least two connecting members extending between each pair of adjacent first and second members, said two connecting members being diametrically opposed and being circumferentially offset from adjacent connecting members.

4. A prosthesis as defined in claim 3, wherein connecting members between a pair of adjacent first and second members are offset by an angle of 90° from adjacent connecting members.

5. A prosthesis as defined in claim 3, wherein said connecting members of said first and second members extend collinearly to and between connecting elements extending within each of said first and second elements for limiting longitudinal expansion or contraction of said prosthesis during radial expansion and deployment thereof.

6. A prosthesis as defined in claim 1, wherein a side opening is defined laterally in at least two adjacent ring-shaped members of said prosthesis for positioning substantially at an ostium of an other body passageway which communicates with the body passageway receiving said prosthesis, a second prosthesis being provided for positioning in said other body passageway and at least partly into said side opening of said prosthesis.

7. An expandable prosthesis for a body passageway comprising at least three ring-shaped members interconnected in a tubular configuration along a longitudinal axis, adjacent ones of the ring-shaped members being flexibly connected together by at least two diametrically opposed connecting members provided between each pair of said adjacent ones of the ring-shaped members for allowing said pairs to be articulated out of coaxial alignment, said connecting members between each said pair of adjacent ring-shaped members being angularly offset from adjacent ones of said connecting members, said ring-shaped members each having longitudinally opposed first and second edges elongate longitudinally aligned connecting elements, said ring-shaped elements each having a collapsed diameter for permitting delivery thereof in the body passageway and each having at least one expanded diameter upon application from the interior of said at least three ring-shaped members of an outwardly directed force for expanding the body passageway, wherein said connecting members extend collinearly to and between at least some of said connecting elements of said ring-shaped elements for limiting longitudinal expansion or contraction of said prosthesis during radial expansion and deployment thereof.

8. A prosthesis as defined in claim 7, wherein a side opening is defined laterally in at least one ring-shaped member of said prosthesis for positioning substantially at an ostium of an other body passageway which communicates with the body passageway receiving said prosthesis, a second prosthesis being provided for positioning in said other body passageway and at least partly into said side opening of said prosthesis.

9. A prosthesis as defined in claim 7, wherein said side opening is defined in at least two adjacent ring-shaped members.

10. A generally tubular stent which is formed from a deformable material and consists of a plurality of ring-shaped elements of the same radius joined together along a common axis, wherein adjacent ring elements each comprise at least two generally circumferential bands such that the ring element extends axially between a first end band and a second end band which are joined together by connectors extending between them, with all of the bands having the same generally zigzag shape having at least three apices and three troughs with respect to a longitudinal direction of the stent around the circumference of the band, wherein the apices and troughs of adjacent first band of one ring element and second band of adjacent ring element are aligned on a straight line parallel to the axis, two adjacent ring elements being joined only by a pair of links arranged generally parallel to the axis, the pair of links being radially spaced by an angle of about 180°, the pair of links to one end of each ring element being positioned radially at an angle in the range of 60° to 120° with respect to the pair of, links joined to the other adjacent rings element, and wherein adjacent bands within each ring are arranged with apices of one and troughs of the other coinciding on a line parallel with the axis, the adjacent bands being joined along said line each of the apices of one band to the respective trough of the adjacent band of the ring element, or vice-versa, whereby the connectors and the portion of adjacent bands joined to connectors form a hexagonal shape with all hexagonal shapes between a pair of adjacent bands having all internal angles less than 180° or having two opposite corners defined by the bands having internal angles greater than 180° and the remaining corners having angles less than 90°.

11. A stent according to claim 10 in which each ring element consists of a pair of bands joined together by respective connectors.

12. A stent according to claim 11 in which ring elements formed of bands joined by connectors to make hexagons having all internal angles less than 180° alternate with ring elements formed as hexagons including two internal angles greater than 180°.

13. A stent according to claim 10 in which a ring element consists of four bands, with two adjacent bands forming regular ;hexagons with their respective connectors and with the other pair of adjacent bands forming inverted hexagons or with the other pair of adjacent bands forming regular hexagons.

14. A stent according to claim 10 in which the pair of links joining an adjacent ring element is angled at 90° to the pair of links joining the the other adjacent ring element.

* * * * *

UNITED STATES PATENT AND TRADEMARK OFFICE
CERTIFICATE OF CORRECTION

PATENT NO.    : 6,520,987 B1
DATED         : February 18, 2003
INVENTOR(S)   : Sylvain Plante It is certified that error appears in the above-identified patent and that said Letters Patent is hereby corrected as shown below:

<u>Column 14,</u>
Lines 30 thru 35, replace Claim 13 as follows:
-- A stent according to claim 10 in which a ring element consists of four bands, with two adjacent bands forming regular hexagons with their respective connectors and with the other pair of adjacent bands forming inverted hexagons or with the other pair of adjacent bands forming regular hexagons. --

Lines 35 thru 38, replace Claim 14 as follows:
-- A stent according to claim 10 in which the pair of links joining an adjacent ring element is angled at 90º to the pair of links joining the other adjacent ring elements. --

Signed and Sealed this

Second Day of September, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,520,987 B1
DATED : February 18, 2003
INVENTOR(S) : Sylvain Plante It is certified that error appears in the above-identified patent and that said Letters Patent is hereby corrected as shown below:

<u>Columns 12-14,</u>
Kindly amend Claims 7, 10, 13 and 14 as follows:

7. An expandable prosthesis for a body passageway comprising at least three ring-shaped members interconnected in a tubular configuration along a longitudinal axis, adjacent ones of the ring-shaped members being flexibly connected together by at least two diametrically opposed connecting members provided between each pair of said adjacent ones of the ring-shaped members for allowing said pairs to be articulated out of coaxial alignment, said connecting members between each said pair of adjacent ring-shaped members being angularly offset from adjacent ones of said connecting members, said ring-shaped members each having longitudinally opposed first and second edges interconnected by elongate longitudinally aligned connecting elements, said ring-shaped elements each having a collapsed diameter for permitting delivery thereof in the body passageway and each having at least one expanded diameter upon application from the interior of said at least three ring-shaped members of an outwardly directed force for expanding the body passageway, wherein said connecting members extend collinearly to and between at least some of said connecting elements of said ring-shaped elements for limiting longitudinal expansion or contraction of said prosthesis during radial expansion and deployment thereof.

10. A generally tubular stent which is formed from a deformable material and consists of a plurality of ring-shaped elements of the same radius joined together along a common axis, wherein adjacent ring elements each comprise at least two generally circumferential bands such that the ring element extends axially between a first end band and a second end band which are joined together by connectors extending between them, with all of the bands having the same generally zigzag shape having at least three apices and three troughs with respect to a longitudinal direction of the stent around the circumference of the band, wherein the apices and troughs of adjacent first band of one ring element and second band of adjacent ring element are aligned on a straight line parallel to the axis, two adjacent ring elements being joined only by a pair of links arranged generally parallel to the axis, the pair of links being radially spaced by an angle of about 180°, the pair of links to one end of each ring element being positioned radially at an angle in the range of 60° to 120° with respect to the pair of links joined to the other adjacent ring element, and wherein adjacent bands within each ring are arranged with apices of one and troughs of the other coinciding on a line parallel with the axis, the adjacent bands being joined along said line each of the apices of one band to the respective trough of the adjacent band of the ring element, or vice-versa, whereby the connectors and the portion of adjacent bands joined to connectors form a hexagonal shape with all hexagonal shapes between a pair of adjacent bands having all internal angles less than 180° or having two opposite corners defined by the bands having internal angles greater than 180° and the remaining corners having angles less than 90°.

UNITED STATES PATENT AND TRADEMARK OFFICE
CERTIFICATE OF CORRECTION

PATENT NO.    : 6,520,987 B1
DATED         : February 18, 2003
INVENTOR(S)   : Sylvain Plante It is certified that error appears in the above-identified patent and that said Letters Patent is hereby corrected as shown below:

13.   A stent according to claim 10 in which a ring element consists of four bands, with two adjacent bands forming regular ;hexagons with their respective connectors and with the other pair of adjacent bands forming inverted hexagons or with the other pair of adjacent bands forming regular hexagons.

14.   A stent according to claim 10 in which the pair of links joining an adjacent ring element is angled at 90° to the pair of links joining the the other adjacent ring element.

Signed and Sealed this

Sixteenth Day of December, 2003

JAMES E. ROGAN
*Director of the United States Patent and Trademark Office*